(12) United States Patent
Rice et al.

(10) Patent No.: US 7,674,612 B2
(45) Date of Patent: Mar. 9, 2010

(54) INFECTIOUS, CHIMERIC HEPATITIS C VIRUS, METHODS OF PRODUCING THE SAME AND METHODS OF USE THEREOF

(75) Inventors: Charles Rice, New York, NY (US); Brett D Lindenbach, New York, NY (US); Matthew J Evans, New York, NY (US); Christopher Jones, New York, NY (US)

(73) Assignee: The Rockefeller University, New York, NY (US)

( * ) Notice: Subject to any disclaimer, the term of this patent is extended or adjusted under 35 U.S.C. 154(b) by 476 days.

(21) Appl. No.: 11/366,839

(22) Filed: Mar. 3, 2006

(65) Prior Publication Data

US 2006/0210969 A1 Sep. 21, 2006

Related U.S. Application Data

(60) Provisional application No. 60/658,187, filed on Mar. 4, 2005.

(51) Int. Cl.
C12N 15/09 (2006.01)
C12N 15/51 (2006.01)
C12N 7/00 (2006.01)
C12N 7/01 (2006.01)
C12N 7/04 (2006.01)
C07H 21/00 (2006.01)
C12N 15/00 (2006.01)

(52) U.S. Cl. .................. 435/235.1; 435/41; 435/69.1; 435/239; 435/320.1; 536/23.7; 536/23.72

(58) Field of Classification Search .................. None
See application file for complete search history.

(56) References Cited

U.S. PATENT DOCUMENTS

| 6,127,116 | A | 10/2000 | Rice et al. |
| 7,049,428 | B1 | 5/2006 | Rice, III et al. |
| 7,084,266 | B1 | 8/2006 | Yanagi et al. |
| 2008/0032323 | A1 * | 2/2008 | Wakita et al. ............ 435/29 |

FOREIGN PATENT DOCUMENTS

| EP | 1801209 | 6/2007 |
| JP | 2004243975 | 9/2004 |
| JP | 2004290801 | 10/2004 |
| JP | 2005069527 | 3/2005 |
| JP | 2005069725 | 3/2005 |
| WO | 03085084 | 10/2003 |
| WO | 2006022422 | 3/2006 |

OTHER PUBLICATIONS

Pietschmann et al., "Construction and characterization of infectious intragenotypic and intergenotypic hepatitis C virus chimeras," Proceedings of the National Academy of Sciences, USA, vol. 103 No. 19, pp. 7408-7413 (May 2006).*

Yi et al., "Compensatory Mutations in E1, p7, NS2, and NS3 Enhance Yields of Cell Culture-Infectious Intergenotypic Chimeric Hepatitis C Virus," Journal of Virology, vol. 81 No. 2, pp. 629-638 (Jan. 2007).*

Kato et al., "Sequence Analysis of Hepatitis C Virus Isolated From a Fulminant Hepatitis Patient," Journal of Medical Virology, vol. 64 No. 3, pp. 334-339 (Jul. 2001).*

Genbank AB047639, "Hepatitis C virus gene for polyprotein, complete cds, clone:JFH-1.," version of Aug. 2001.*

GenBank D00944, "Hepatitis C virus genomic RNA for polyprotein, complete cds," version Jun. 1998.*

GenBank AF009606, "Hepatitis C virus polyprotein gene, complete cds.," version Aug. 1997.*

Alignment of nucleic acids 1-300 of SEQ ID No. 5, Jul. 2008.*
Alignment of nucleic acids 301-3430 of SEQ ID No. 5, Jul. 2008.*
Alignment of nucleic acids 3431-9666 of SEQ ID No. 5, Jul. 2008.*
Alignment of nucleic acids 301-3430 of SEQ ID No. 1, Jul. 2008.*

Berke et al., "Hepatitis C virus comes full circle: Production of recombinant infectious virus in tissue culture," Hepatology, vol. 42 No. 6, pp. 1264-1269 (Dec. 2005).*

Scheel et al., "Development of JFH1-based cell culture systems for hepatitis C virus genotype 4a and evidence for cross-genotype neutralization," Proceedings of the National Academy of Sciences, USA, vol. 105 No. 3, pp. 997-1002 (Jan. 2008).*

Blight et al., "Efficient initiation of HCV RNA replication in cell culture." Science. Dec. 8, 2000;290(5498):1972-4.

Yanagi et al., "Hepatitis C virus: an infectious molecular clone of a second major genotype (2a) and lack of viability of intertypic 1a and 2a chimeras." Virology. Sep. 15, 1999;262(1):250-63.

Lindenbach et al., "Complete replication of hepatitis C virus in cell culture." Science. Jul. 22, 2005;309(5734):623-6.

Pietschmann et al., "Persistent and transient replication of full-length hepatitis C virus genomes in cell culture." J Virol. Apr. 2002;76(8):4008-21.

Date et al., "Genotype 2a hepatitis C virus subgenomic replicon can replicate in HepG2 and IMY-N9 cells." J Biol Chem. May 21, 2004;279(21):22371-6.

Kato et al., "Efficient replication of the genotype 2a hepatitis C virus subgenomic replicon." Gastroenterology. Dec. 2003;125(6):1808-17.

Lohmann et al., "Replication of subgenomic hepatitis C virus RNAs in a hepatoma cell line." Science. Jul. 2, 1999;285 (5424):110-3.

Blight et al., "Highly permissive cell lines for subgenomic and genomic hepatitis C virus RNA replication." J Virol. Dec. 2002;76(24):13001-14.

(Continued)

*Primary Examiner*—Zachariah Lucas
(74) *Attorney, Agent, or Firm*—Thompson Coburn LLP; Charles P. Romano

(57) ABSTRACT

The present invention provides infectious recombinant Hepatitis C Viruses (HCV), and vectors, cells and animals comprising the same. The present invention provides methods of producing infectious recombinant HCV, and their use in identifying anti-HCV therapeutic agents, as well as sequences of HCV associated with HCV pathogenesis.

31 Claims, 9 Drawing Sheets

OTHER PUBLICATIONS

Bukh et al., "Mutations that permit efficient replication of hepatitis C virus RNA in Huh-7 cells prevent productive replication in chimpanzees." PNAS 2002;99;14416-14421.

Blight et al., "Efficient Replication of Hepatitis C Virus Genotype 1a RNAs in Cell Culture" J. Virol. 2003; vol. 77 (5):3181-3190.

International Search Report and Written Opinion of the International Searching Authority for Corresponding PCT/US2006/007454, Jun. 2008.

Pietschmann et al.; "Chimeric Hepatitis C Virus Infectious in Cell Culture"; Paper presented at the 11th International Symposium on HCV and Related Viruses; Oct. 5, 2004; Heidelberg, Germany.

Lohmann et al.; "Mutations in Hepatitis C Virus RNAs Conferring Cell Culture Adaptation"; Journal of Virology; Feb. 2001; pp. 1437-1449; vol. 75, No. 3.

Lemm et al.; "Replication-Competent Chimeric Hepatitis C Virus Subgenomic Replicons"; Intervirology; 2005; pp. 183-191; vol. 48.

Gu et al.; "Replication Studies Using Genotype 1a Subgenomic Hepatitis C Virus Replicons"; Journal of Virology; May 2003; pp. 5352-5359; vol. 77, No. 9.

European Search Report for Corresponding EP Application No. 06736723.5 dated Sep. 25, 2009.

Heller et al., "An In Vitro Model of Hepatitis C Virion Production", Proceedings of the National Academy of Sciences of USA, Feb. 8, 2005, pp. 2579-2583, vol. 102, No. 7, National Academy of Science, Washington, DC, US.

Kalinina et al., "A Natural Intergenotypic Recombinant of Hepatitis C Virus Identified in St. Petersburg", Journal of Virology, The American Society for Microbiology, Apr. 1, 2002, pp. 4034-4043, vol. 76, No. 8.

Kaul et al., "Cell Culture Adaptation of Hepatitis C Virus and In Vivo Viability of an Adapted Variant", Journal of Virology, Dec. 1, 2007, pp. 13168-13179, vol. 81, No. 23, The American Society for Microbiology, US.

Wakita et al., "Production of Infectious Hepatitis C Virus in Tissue Culture from a Cloned Viral Genome", Nature Medicine, Jul. 1, 2005, pp. 791-796, vol. 11, No. 7, Nature Publishing Group, New York, NY, US.

Zhong et al., "Robust Hepatitis C Virus Infection in Vitro", Proceedings of the National Academy of Sciences of USA, Jun. 1, 2005, pp. 9294-9299, vol. 102, No. 26, National Academy of Science, Washington, DC, US.

Pietschmann et al., "Construction and Characterization of Infectious Intragenotypic and Intergenotypic Hepatitis C Virus Chimeras", National Academy of Science, Washington, DC, US, May 9, 2006, pp. 7408-7413, vol. 103, No. 19, Proceedings of the National Academy of Sciences of USA.

\* cited by examiner

| Inhibitor | IC50 (nM) observed for HCVcc | reported 1b replicons |
|---|---|---|
| 2' C-methyladenosine | 30 | 300 |
| BILN 2061 | 200 | 3 |
| PI-1 | 400 | 60 |
| SCH6 | 300 | 100 |

A

B

INFECTIOUS, CHIMERIC HEPATITIS C VIRUS, METHODS OF PRODUCING THE SAME AND METHODS OF USE THEREOF

CROSS REFERENCE TO RELATED APPLICATIONS

This application claims the priority of U.S. Provisional Application Ser. No. 60/658,187 filed Mar. 4, 2005, which is incorporated herein by reference in its entirety.

GOVERNMENT INTEREST STATEMENT

This invention was made in whole or in part with government support under grant number CA 579373, awarded by the National Institute of Health. The government may have certain rights in the invention.

FIELD OF THE INVENTION

This invention provides infectious recombinant hepatitis C viruses (HCV), and vectors, cells and animals comprising the same. The present invention provides methods of producing the infectious recombinant HCV, and their use in identifying anti-HCV therapeutic and including for use in vaccines and diagnostics and, as well as sequences of HCV associated with HCV pathogenesis.

BACKGROUND OF THE INVENTION

Hepatitis C virus (HCV) is a member of the Flaviviridae family of enveloped, positive-strand RNA viruses and constitutes the type member of the genus *Hepacivirus*. HCV contains a 5' uncapped positive strand RNA genome of 9.4 kb, that possesses two overlapping open reading frames: one is translated into a single polyprotein of 3010 amino acids, while the other yields a 17 kDa protein. The viral polyprotein is processed to generate at least 10 different structural and nonstructural proteins. The genome of HCV is highly heterogeneous and the virus circulates as quasispecies in a single infected individual. HCV is primarily hepatotropic, but it has also been implicated in lymphoproliferative diseases such as mixed cryoglobulinaemia, B-cell non-Hodgkin's lymphoma, and Sjögren's syndrome.

HCV is a significant pathogen, with nearly 3% of the world's population, roughly 170 million people, persistently infected. HCV is a significant etiologic agent of chronic liver disease. About 85% of primary infections become chronic, and ~20% of patients with chronic HCV develop serious complications, such as liver cirrhosis, end-stage liver disease, hepatocellular carcinoma, and death due to liver failure.

The search for HCV drugs as well as for the development of an HCV vaccine is severely hampered by the lack of an efficient tissue culture, or robust cellular system that would support virus replication, or a simple animal system for the study of replication and HCV pathogenicity. The only animal models currently available for the study of this virus are the chimpanzee and a mouse that possesses a chimeric human liver.

Some vitro culture systems attempted for the study of HCV used human cells of hepatocytic and lymphocytic origin, but low and variable levels of replication and virus-induced cytotoxicity posed important problems. Primary hepatocytes (derived from a human donor) can be infected with HCV isolated from serum of infected patients, and the virus can be detected in the supernatant for several weeks after infection, however, the availability of primary hepatocytes is limited and, their isolation is time-consuming and labor-intensive. Consequently, such tissue culture systems are generally considered unsuitable for intensive large-scale antiviral studies.

Another example of a culture system is human hepatoma cells transfected with a vector comprising subgenomic selective replicons cloned from a full-length HCV consensus genome from an infected liver. The proposed system was limited, however, by the fact that only non-structural viral proteins were expressed.

There thus remains a need to provide a culture system that would enable the study of HCV replication and/or pathogenesis and the development of a treatment or prophylaxis for HCV infections.

SUMMARY OF THE INVENTION

The invention provides, in one embodiment, an isolated nucleic acid molecule encoding an infectious recombinant HCV genome, which nucleic acid comprises a chimeric HCV genome.

In one embodiment, the chimeric HCV genome comprises sequences encoding structural genes (core, E1, E2) and non-structural genes p7 and NS2 from a first HCV strain, and sequences encoding a 5' non-coding region (NCR), nonstructural genes NS3, NS4A, NS4B, NS5A, NS5B, and 3' NCR from a second HCV strain. In one embodiment, the first HCV strain and the second HCV strain are from different genotypes. In one embodiment, the first HCV strain is strain J6, and in another embodiment, the second HCV strain is strain JFH1. In one embodiment, the nucleic acid comprises a sequence as set forth in SEQ ID NO: 1 and/or 2 and/or 3 and/or 4 and/or 5. In another embodiment, the nucleic acid comprises a sequence sharing at least 90% identity with that set forth in SEQ ID NO: 1 and/or 2 and/or 3 and/or 4 and/or 5. In one embodiment, the nucleic acid comprises a sequence, which encodes for an H2476L mutation in the NS5B protein, a S1107T mutation in the NS3 protein, or a combination thereof. In another embodiment, the nucleic acid encodes for a K12N mutation in the core protein, an I348S mutation or A269T mutation in the E1 protein, or combinations thereof. In another embodiment, the nucleic acid further comprises a reporter gene, which, in one embodiment, is a gene encoding neomycin phosphotransferase, *Renilla* luciferase, secreted alkaline phosphatase (SEAP), Gaussia luciferase or the green fluorescent protein.

In another embodiment, the invention provides an animal, or in another embodiment, a viral particle, or in another embodiment a vector, or in another embodiment, a cell comprising the isolated nucleic acid molecule of the invention. In one embodiment, the cell is a hepatocyte, or in another embodiment, the cell is of the Huh-7 or Huh-7.5 cell line.

In one embodiment, the invention provides a method for producing infectious HCV, comprising contacting a cell with an isolated nucleic acid molecule encoding an infectious recombinant HCV genome, which nucleic acid comprises a chimeric HCV genome.

In one embodiment, the infectious HCV is obtained at a titer of $10^1$-$10^6$ TCID$_{50}$/ml. In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots. In another embodiment, the method comprises culturing the cell in a media comprising N-acetylcysteine, at a concentration of about at least 5 mM.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic. In one embodiment, the candidate molecule is an antibody, or in another embodiment, a nucleic acid.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus indicates that the HCV variant has improved growth in cell culture.

According to this aspect of the invention, and in one embodiment, the HCV variants are selected for enhanced replication, over a long course of time, in in vitro culture systems. In one embodiment, the cells contacted with the variants are characterized by reduced infection, as compared to cells contacted with the chimeric HCV.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus indicates the mutation is in an HCV sequence associated with HCV pathogenicity.

DETAILED DESCRIPTION OF THE INVENTION

Figure 1:
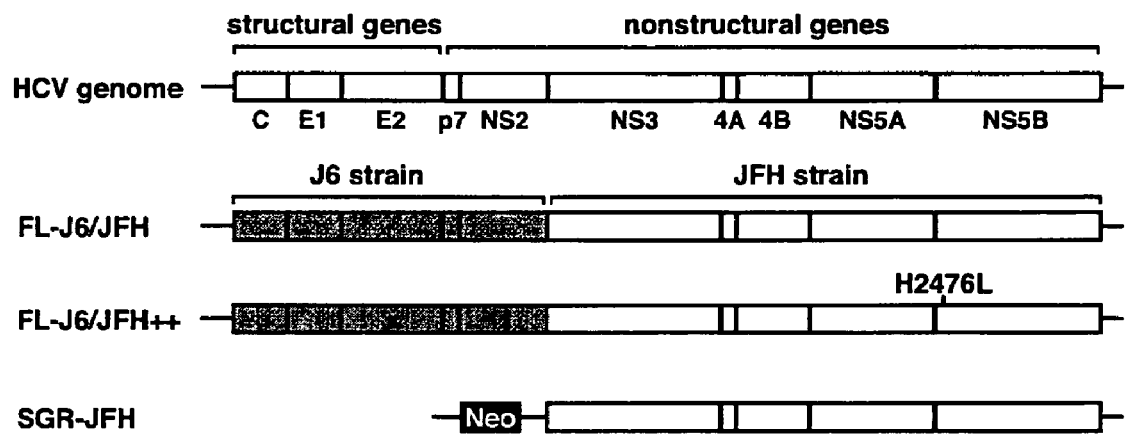
FIG. 1 schematically depicts the constructs. The full-length genotype 2a chimeric HCV genomes FL-J6/JFH and FL-J6/JFH++ are illustrated. For comparison, the SGR-JFH subgenomic replicon is also shown.

The genome of Flaviviridae represents a single-stranded, unsegmented RNA molecule of positive polarity. Following infection and uncoating, the viral genome operates as a messenger RNA in the cytoplasm of the host cell. Translation leads to the synthesis of an unstable polyprotein that is co- and post-translationally processed by cellular as well as viral proteases to give rise to the virus structural and non-structural proteins. The structural proteins constitute the virus particle, where the virion is composed of a capsid and a membrane envelope, the latter which contains two to three membrane-associated viral envelope proteins. The non-structural proteins, which are predominantly generated by the activity of well-characterized viral proteases, are thought to act as catalytic components of the viral multiplication machinery. Virus-encoded enzymatic functions, beyond that of the viral proteases, which are essentially involved in the RNA replication process, include an RNA helicase and/or a nucleoside triphosphatase and an RNA-dependent RNA polymerase (RdRp) activity.

This invention provides, in one embodiment, an isolated nucleic acid molecule encoding an infectious recombinant HCV genome, which nucleic acid comprises a chimeric HCV genome.

In one embodiment, the term "nucleic acid" refers to polynucleotide or to oligonucleotides such as deoxyribonucleic acid (DNA), and ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotide. This term includes oligonucleotides composed of naturally occurring nucleobases, sugars and covalent intemucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the term "chimeric" refers to an isolated nucleic acid, or construct or virus or viral particle of this invention, resulting from the combination of genes from two or more different sources, in which the different parts of the chimera function together. The genes are fused, where necessary in-frame, in a single genetic construct. In one embodiment, the term "chimeric" refers to recombinant HCV-derived nucleic acids or vectors or virus, or viral particles wherein the genome of the HCV within these nucleic acids or vectors or virus, or viral particles is modified such that there is an insertion or substitution of sequences, in addition to the incorporation of sequences comprising the HCV genome from at least two HCV genomes, subtypes, quasispecies or strains.

In some embodiments, the genome is a chimera of any combination of HCV 1, 2, 3, 4, 5, 6, 7, 8, 9, 10 or 11 genotypes. In one embodiment, the genome is a chimera of any combination of HCV genome subtypes 1a, 1b, 1c, 2a, 2b, 2c, 3a, 3b, 4a, 4b, 4c, 4d, 4e, 5a, 6a, 7a, 7b, 8a, 8b, 9a, 10a, 11a, such that chimeras may comprise nucleic acids of the same HCV genotype, but different subtype, in some embodiments. In other embodiments, the nucleic acids chimeras are of different genotype.

In one embodiment, the isolated nucleic acid may be used to produce an infectious virus. In one embodiment, the term "infectious" refers to the ability of a virus to enter and replicate in a cell and to produce viral particles. Infectivity can be evaluated either by detecting virus, i.e., viral load, or by observing disease progression in an animal. Virus (viral load) can be detected by the presence of viral (+) strand RNAs and/or (−) strand replication intermediates, e.g., detected by RT-PCR or direct hybridization techniques. It can also be detected, if present in sufficient amount, by the presence of replicon-derived proteins, e.g., detected by immunoassay or biochemical techniques. In another alternative, a culture medium isolated from a cell line supporting viral replication or extracts/samples from an animal are used to infect naive cells in culture. In another embodiment, infectivity may be determined in vivo (i.e., in infected animals) and the isolated nucleic acids, vectors, viruses, viral particles and methods of this invention enable the development of an acute or, in another embodiment, chronic viral infection model, which, may include either overt pathology or replication and propagation of the virus.

In one embodiment, the invention provides a recombinant HCV, or viral particle comprising an isolated nucleic acid of this invention.

In one embodiment, the term "hepatitis C virus" or "HCV" refers to a viral species of which pathogenic strains cause hepatitis C, or in another embodiment, refers to non-A, non-B hepatitis. In one embodiment, the "viral particle" refers to a preparation of HCV viral or virus-like particles of this invention, that have been isolated from the cellular constituents with which the virus associates, and from other types of viruses that may be present in the infected tissue. The techniques for isolating viruses and/or particles of this invention are known to those of skill in the art, and include, for example, centrifugation and affinity chromatography.

In one embodiment, the "recombinant HCV virus genome" is a DNA molecule that has undergone a molecular biological manipulation, to yield a genome comprising the desired sequences.

In one embodiment, the chimeric HCV genome comprises sequences encoding structural genes (core, E1, E2) and non-structural genes p7 and NS2 from a first HCV strain, and sequences encoding a 5' non-coding region (NCR), nonstructural genes NS3, NS4A, NS4B, NS5A, NS5B, and 3' NCR from a second HCV strain.

In one embodiment, the first HCV strain is J6 or in another embodiment H77, while the second HCV strain in both is JFH1.

In one embodiment, the nucleic acid comprises a sequence as set forth in SEQ ID NO: 1 and/or 2 and/or 3 and/or 4 and/or 5. In another embodiment, the nucleic acid comprises a sequence sharing at least 90% identity with that set forth in SEQ ID NO: 1 and/or 2 and/or 3 and/or 4 and/or 5.

In one embodiment, the invention provides a nucleic acid molecule comprising a sequence homologous to that set forth in SEQ ID NO: 1 and/or 2 and/or 3 and/or 4 and/or 5.

In one embodiment, the terms "homology", "homologue" or "homologous", refer to a molecule, which exhibits, in one embodiment at least 70% correspondence with the indicated molecule, in terms of, in one embodiment, its structure, or in another embodiment, amino acid sequence. In another embodiment, the molecule exhibits at least 72% correspondence with the indicated sequence or structure. In another embodiment, the molecule exhibits at least 75% correspondence with the indicated sequence or structure. In another embodiment, the molecule exhibits at least 80% correspondence with the indicated sequence or structure. In another embodiment, the molecule exhibits at least 82% correspondence with the indicated sequence or structure. In another embodiment, the molecule exhibits at least 85% correspondence with the indicated sequence or structure. In another embodiment, the molecule exhibits at least 87% correspondence with the indicated sequence or structure. In another embodiment the molecule exhibits at least 90% correspondence with the indicated sequence or structure. In another embodiment, the molecule exhibits at least 92% correspondence with the indicated sequence or structure. In another embodiment, the molecule exhibits at least 95% or more correspondence with the indicated sequence or structure. In another embodiment, the molecule exhibits at least 97% correspondence with the indicated sequence or structure. In another embodiment, the molecule exhibits at least 99% correspondence with the indicated sequence or structure. In another embodiment, the molecule exhibits 95%-100% correspondence with the indicated sequence or structure. Similarly, as used herein, the reference to a correspondence to a particular molecule includes both direct correspondence, as well as homology to that molecule as herein defined.

Homology, as used herein, may refer to sequence identity, or may refer to structural identity, or functional identity. By using the term "homology" and other like forms, it is to be understood that any molecule, that functions similarly, and/or contains sequence identity, and/or is conserved structurally so that it approximates the reference molecule, is to be considered as part of this invention.

In one embodiment, the nucleic acid comprises a sequence encoding for a H2476L mutation in the NS5B protein, a S1107T mutation in the NS3 protein, a K12N mutation in the core protein, an I348S mutation or A269T mutation in the E1 protein, or combinations thereof.

In one embodiment, the mutation refers to at least one nucleotide change, which occurs, or is engineered to occur within the sequence. Such mutated engineered viruses are also referred to as variants, in one embodiment. In one embodiment, the mutation produces a change of one or more nucleotides in a given codon position, yet results in no alteration in the amino acid encoded at that position. In another embodiment, the mutation results in a given amino acid residue in a protein or enzyme being changed without altering the overall conformation and function of the polypeptide, including, but not limited to, replacement of an amino acid with one having similar properties (such as, for example, polarity, hydrophobicity, size of the side chain, hydrogen bonding potential, and the like).

In another embodiment, mutations are introduced in the isolated nucleic acids, vectors, viruses and viral particles of this invention, in order to alter the properties of the virus. In one embodiment, mutations are introduced in order to produce an HCV virus which has greater longevity, infectivity, replication, or is in any way more amenable to propagation in culture.

In another embodiment, mutations are introduced in order to attenuate HCV pathogenicity. Such mutated nucleic acids, vectors, viruses and viral particles of this invention, may also be used as vaccines for inhibiting HCV infection or pathogenesis.

In another embodiment, mutations are introduced, which result in greater pathogenicity of HCV. According to this aspect, and in one embodiment, such mutations may be desirable in order to delineate pathogenic mechanisms of HCV. For example, the mutation may result in aggressive neoplasia, when administered to an animal model, such that mechanisms of HCV-mediated neoplasia may be more readily studied, and treatment protocols or therapeutic compounds may be evaluated.

In one embodiment, the term "pathogenesis" refers to disease progression, or in another embodiment, to the pathogenic effects of viral infection, or, in another embodiment, morbidity or in another embodiment, mortality as a result of HCV contact with a host.

In another embodiment, the nucleic acid further comprises a reporter gene, which, in one embodiment, is a gene that encodes neomycin phosphotransferase, *Renilla* luciferase, secreted alkaline phosphatase (SEAP), Gaussia luciferase or the green fluorescent protein. In one embodiment, the reporter gene results in a marker that is detectable in supernatants of cultured cells infected with the chimeric constructs of this invention, as exemplified herein below, and as will be appreciated by one skilled in the art.

In another embodiment, the invention provides an animal, or in another embodiment, a viral particle, or in another embodiment a vector, or in another embodiment, a cell comprising the isolated nucleic acid molecule of the invention. In one embodiment, the cell is a hepatocyte, or in another embodiment, the cell is of the Huh-7 or Huh-7.5 cell line.

In one embodiment, the cell, or in another embodiment, cell systems of this invention comprise primary cultures or cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

In one embodiment, the invention provides a method for producing infectious HCV, comprising contacting a cell with an isolated nucleic acid molecule encoding an infectious recombinant HCV genome, which nucleic acid comprises a chimeric HCV genome.

In order to generate the nucleic acid constructs of the present invention disclosed herein, polynucleotide segments can be ligated into commercially available expression construct systems suitable for transforming bacterial cells or mammalian cells, as will be known to one skilled in the art. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides, and as such, encompass other embodiments of the present invention.

In some embodiments of the present invention the construct may comprise, a virus, a plasmid, a bacmid, a phagemid, a cosmid, or a bacteriophage.

Nucleotide sequences are typically operably linked to, i.e., positioned, to ensure the functioning of an expression control sequence. These expression constructs may be replicable in the cells either as episomes or as an integral part of the cell's chromosomal DNA, depending upon the desired application. In one embodiment, the expression constructs contain selection markers, such as for example, drug resistance cassettes or reporter proteins, which facilitate detection and/or selection of cells transformed/transduced with the desired nucleic acid sequences (see, e.g., U.S. Pat. No. 4,704,362). These markers, however, are not exclusionary, and numerous others may be employed, as known to those skilled in the art. In one embodiment of the present invention, reporter genes utilized may include, inter-alia, β-galactosidase, chloramphenicol acetyl transferase, luciferase or a fluorescent protein.

Figure 2:
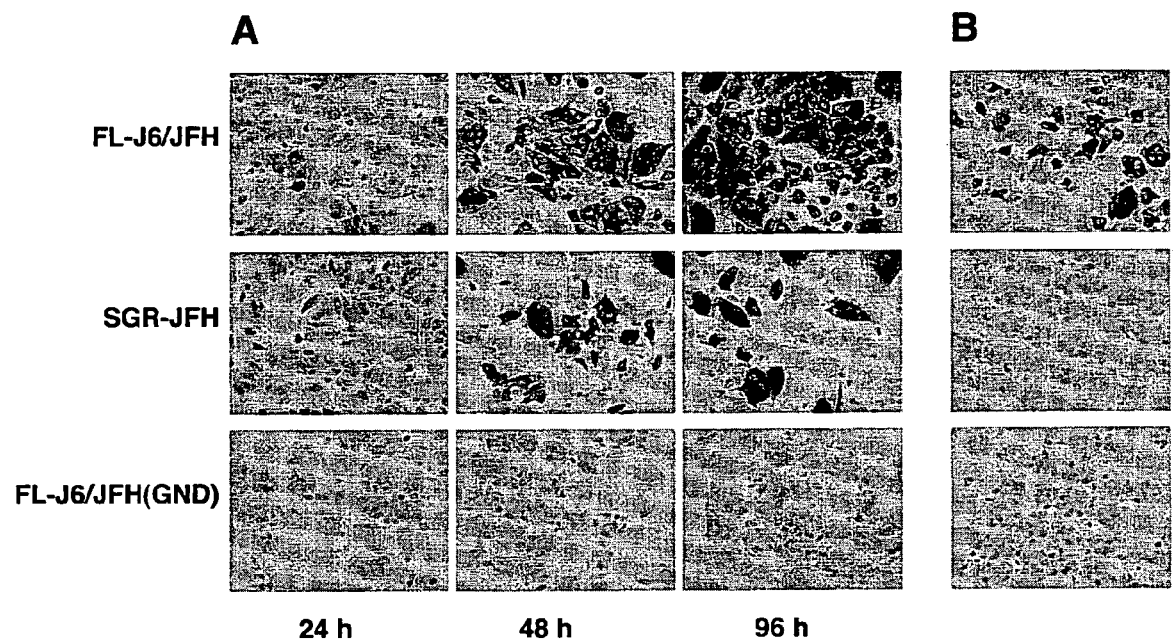
FIG. 2 demonstrates replication and infection of FL-J6/JFH. A) Huh-7.5 cells transfected with FL-J6/JFH, SGR-JFH, or FL-J6/JFH(GND), as indicated, were fixed and immunostained for NS5A at the indicated times post-transfection. NS5A expression appears as a dark brown staining. Cells were counterstaining with hemotoxylin (light blue). B) Conditioned media were recovered from the cells in panel A at 48 hours, clarified by centrifugation and filtration, and incubated with naïve Huh-7.5 cells. Following an additional 48 hours, cells were stained for NS5A expression as above.

The nucleic acids of this invention were in vitro transcribed to produce RNA, which was then used to transfect Huh-7.5 cells, which were found to be more permissive to the chimeric HCV, as compared to the parental cell line. The methods as described, produced infectious viral particles, as seen by infection of naïve cells by supernatant drawn from infected cell cultures (FIG. 2B).

Incorporation of recombinant nucleic acid within cells can be accomplished through a number of methods well known in the art.

Some techniques known in the art for introducing the above described recombinant nucleic acids, viruses, viral particles, or vectors into cells of the present invention, may include, but are not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation, liposome-mediated transfection, direct injection, and receptor-mediated uptake (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Bombardment with nucleic acid coated particles is also envisaged.

Figure 3:
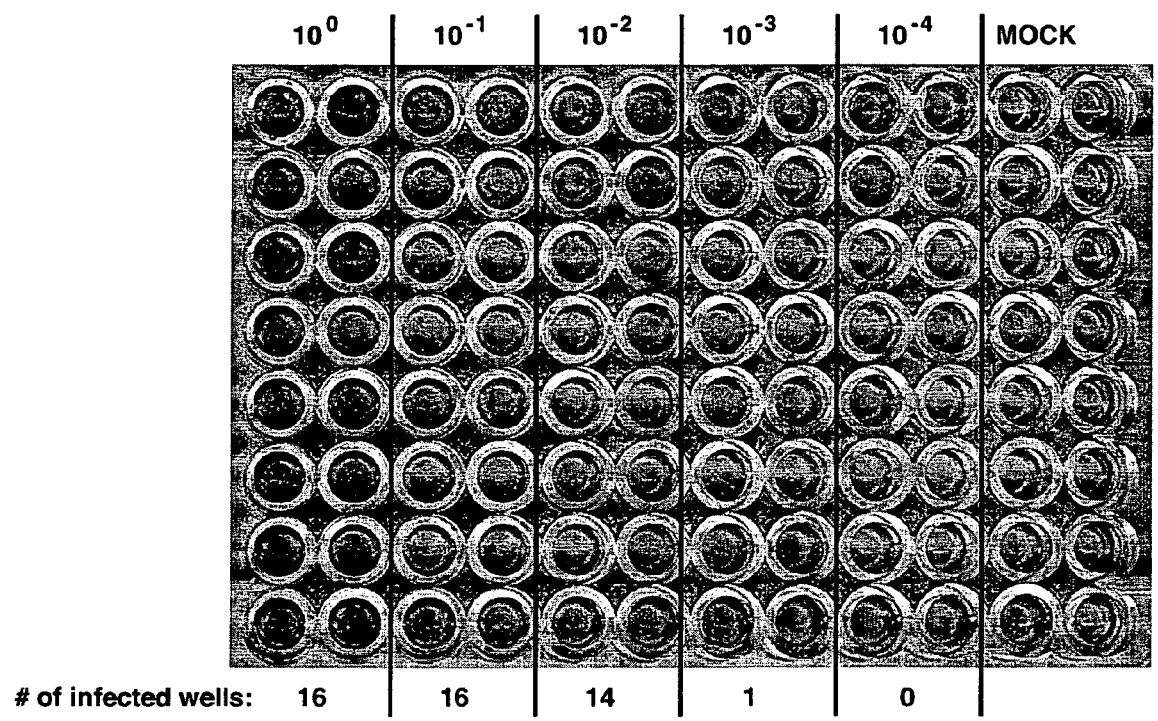
FIG. 3 demonstrates the results of a 50% endpoint dilution assay. Huh-7.5 cells were seeded in a 96 well plate at a density of around $8 \times 10^3$ cells per well. The media were replaced with 0.1 ml/well of the indicated virus dilutions. Three days later, cells were fixed and stained for NS5A as in FIG. 2. The number of infected wells were tabulated for each virus dilution and used to calculate the titer. For this particular virus preparation, the titer was $2.90 \times 10^3$ TCID50/ml.

In one embodiment, the infectious HCV is obtained at a titer of $10^1$-$10^6$ TCID$_{50}$/ml. High viral titers which were infectious and obtainable via the methods of this invention, as seen in, for example, FIG. 3. Standard concentration procedures may be used, in another embodiment, to obtain yet higher titers, as exemplified further herein. In other embodiments, varying the culture conditions optimize production, such as exemplified herein, as seen via the addition of N-acetylcysteine, when supplied to provide a concentration of at least 5 mM, or in another embodiment, at least 20 mM, or in another embodiment, at least 30 mM, etc, in the culture media. In one embodiment, N-acetylcysteine, may be supplied to provide a concentration of about 5-1000 mM, for the methods of this invention.

In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule. In one embodiment, the molecule is labeled for easier detection, including radiolabeled, antibody labeled for fluorescently labeled molecules, which may be detected by any means well known to one skilled in the art.

In one embodiment, the candidate molecule is an antibody.

In one embodiment, the term "antibody" refers to intact molecules as well as functional fragments thereof, such as Fab, $F(ab')_2$, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "$F(ab')_2$", refers to the fragment of the antibody that can be obtained by treating whole antibody with the enzyme pepsin without subsequent reduction, $F(ab')_2$ is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art. (See for example, Harlow and Lane, Antibodies: A Laboratory Manual, Cold Spring Harbor Laboratory, New York, 1988, incorporated herein by reference).

Antibody fragments for use according to the methods of the present invention can be prepared, in one embodiment, through proteolytic hydrolysis of an appropriate antibody, or, in other embodiments, by expression in *E. coli* or mammalian cells (e.g. Chinese hamster ovary cell culture or other protein expression systems) of DNA encoding the fragment.

In some embodiments, antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. In other embodiments, enzymatic cleavage using pepsin can be used to produce two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, in some embodiments, as described in Inbar et al., Proc. Nat'l Acad. Sci. USA 69:2659-62, 1972. In other embodiments, the variable chains can be linked by an intermolecular disulfide bond or cross-linked by chemicals such as glutaraldehyde. In some embodiments, the Fv fragments comprise VH and VL chains connected by a peptide linker. These single-chain antigen binding proteins (sFv) may be prepared by constructing a structural gene comprising DNA sequences encoding the VH and VL domains connected by an oligonucleotide. The structural gene may be inserted into an expression vector, which is subsequently introduced into a host cell such as E. coli. The recombinant host cells may synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which are hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments, may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modeling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

The replication level of a virus can be determined, in other embodiments, using techniques known in the art, and in other embodiments, as exemplified herein. For example, the genome level can be determined using RT-PCR. To determine the level of a viral protein, one can use techniques including ELISA, immunoprecipitation, immunofluorescence, EIA, RIA, and Western blotting analysis. To determine the replication rate of a virus, one can use the method described in, e.g., Billaud et al., Virology 266 (2000) 180-188.

In another embodiment, the inhibition of HCV replication and/or infection and/or pathogenesis includes inhibition of downstream effects of HCV or infection with other Flaviviridae. In one embodiment, downstream effects include neoplastic disease, including, in one embodiment, the development of hepatocellular carcinoma.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an $IC_{50}$ in the range of from about 0.0001 nM to 100 µM in an in vitro assay for at least one step in infection, replication, or pathogenesis of HCV, more preferably from about 0.0001 nM to 75 µM, more preferably from about 0.0001 nM to 50 µM, more preferably from about 0.0001 nM to 25 µM, more preferably from about 0.0001 nM to 10 µM, and even more preferably from about 0.0001 nM to 1 µM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology indicates a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew *Tupaia belangeri chinensis*. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus indicates that the HCV variant has improved growth in cell culture. In some embodiments, HCV variants are selected for enhanced replication, over a long course of time, in in vitro culture systems. According to this aspect of the invention, and in some embodiments, cells contacted with the variants are characterized by reduced infection, as compared to cells contacted with the chimeric HCV.

In some embodiments, the methods are employed to specifically identify and isolate HCV genomes that efficiently replicate intracellularly (RNA replication), but produce moderate to undetectable levels of infectious virus particles. Since HCV RNA replication is extremely error prone, mutations naturally accumulate over time within a population of progeny genomes maintained in culture. According to this aspect, in one embodiment, the method may make use of multiple passaging of cultures transfected with RNAs that do not produce infectious virus, for example detected via assaying NS5A-positivity, over a course of time, and under conditions that allow for accumulation of mutation in the virus. The mutations, according to this aspect, and in one embodiment, arise within the population of replicating HCV RNAs, ultimately resulting in a net increase in NS5A-positive cells over time.

In some embodiments, the invention provides a screening method for identifying HCV isolates which can replicate well in culture. For example, a cell line, such as a derivative of Huh-7 or Huh-7.5 that responds to productive HCVcc infection by expression of a reporter gene, is used to screen clinical samples to identify HCV isolates capable of infection and spread within the cell culture.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus indicates the mutation is in an HCV sequence associated with HCV pathogenicity.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/ vectors/cells/nucleic acids of this invention, for administration to a subject, and is to be considered as part of this invention.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

The following examples are intended to illustrate but not limit the present invention.

EXAMPLES

Materials and Experimental Methods

DNA Constructs

FL-J6/JFH is a full-length, chimeric, genotype 2a HCV genome (FIG. 1) containing the core-NS2 coding region from the J6 HCV isolate (Yanagi, M., et al. 1999. Virology 262: 250-263) and the NS3-NS5B coding region of HCV strain JFH-1 (Kato, T., et al. 2003. Gastroenterology 125:1808-17). This genome includes nucleotides (nt) 1-300 of the JFH-1 strain, nt 301-3430 of the J6 strain, and nt 3431-9678 of the JFH-1 strain. FL-J6/JFH++ is a derivative of FL-J6/JFH that contains a mutation in NS5B, A7767T (H2476L), which has been previously found to enhance replication of the JFH-1 subgenomic replicon (Kato, supra). These genomes were created by using standard molecular biology techniques (Sambrook, J., E. Fritsch, and T. Maniatis. 1989. *Molecular cloning: a laboratory manual*. Cold Spring Harbor Laboratory, Cold Spring Harbor, N.Y.) and were maintained as cloned cDNAs within the plasmids pFL-J6/JFH and pFL-J6/JFH++.

In Vitro Transcription of Infectious RNA pFL-J6/JFH and pFL-J6/JFH++ were linearized with XbaI followed by digestion with Mung Bean Nuclease. DNA templates were then purified by Proteinase K digestion, two rounds of phenol extraction, ethanol precipitation as a sodium salt, and resuspended at 1 mg/ml. Infectious RNAs were synthesized with T7 RNA Polymerase via standard in vitro transcription reactions (Milligan, J. F., and O. C. Uhlenbeck. 1989. Synthesis of small RNAs using T7 RNA polymerase. Methods Enzymol 180:51-62), followed by treatment with DNase I and standard RNA purification methods. For example, RNAs are purified with Qiagen RNeasy Mini columns with on-column DNase I digestion and eluted into 2 mM Sodium Citrate, pH 6.4.

RNA Transfections

Huh-7.5 is a derivative of the human hepatoma line Huh-7 that is highly permissive for HCV RNA replication. Cells were maintained at low passage ($\leq$45) at 37° C. and 5% $CO_2$ in Dulbecco's modified minimal essential medium (DMEM) containing 10% heat-inactivated fetal calf serum and 100 µM nonessential amino acids (herein referred to as complete growth medium). Huh-7.5 (or Huh-7) cells were transfected by using standard techniques (Blight, K. J., et al. 2002. J. Virol. 76:13001-14.). For example, 6×10$^6$ cells in 0.4 ml phosphate-buffered saline (PBS) were electroporated with 1 µg RNA in a 2 mm-gap cuvette by using a BTX ECL 620 electroporator set for 5 pulses of 99 µsec at 820 V, then replated in complete growth medium.

Example 1

Detection of HCV Replication and Spread Using the Culture System

The FL-J6/JFH construct comprises the cloned cDNA of a chimeric HCV genome with the sequence as set forth in SEQ ID No: 1.

Replication of FL-J6/JFH or FL-J6/JFH++ can be monitored by various methods. A standard immunohistochemical staining procedure was adapted to detect NS5A expression in cells by using the 9E10 monoclonal antibody (Dr. Tim Tellinghuisen and Dr. Charles M. Rice). Antibody staining of HCV-positive cells was revealed through the use of a horseradish peroxidase-coupled secondary antibody and diaminobenzidine. As can be seen in FIG. 2A, HCV replication in Huh-7.5 cells transfected with the FL-J6/JFH or the SGR-JFH subgenomic replicon, was detected, however FL-J6/JFH (GND), which contained a lethal mutation in the HCV RNA polymerase active site was not detected.

Cells harboring FL-J6/JFH secreted infectious virus particles (HCVcc) that were capable of transferring NS5A expression to naïve cells (FIG. 2B). Controls showed that expression of NS5A was not transferred by conditioned media from the subgenomic replicon, which lacks the viral structural genes, or cells transfected with the non-replicating full-length genome (FIG. 2B). Furthermore, infection of naïve cells was retained in the supernatant after centrifugation (5000×g for 30 min) and passage through a 0.2 µm filter (FIG. 2B), which are consistent with infection by a virus.

In another method, HCV RNA levels were monitored by a Taqman assay developed for detecting genotype 2a sequences. This assay showed that ≈10$^5$ copies of HCV RNA were present in 10 ng of Huh-7.5 RNA, 48 hours postinfection, while naïve cells showed undetectable HCV RNA levels (limit of detection ≈500 RNA copies/10 ng).

Huh7.5 cells were found to be more permissive for replication and spread of HCVcc than Huh-7 cells.

Example 2

Quantitation of HCV Infectivity

The procedure for immunohistochemical staining for NS5A has been adapted to determine the infectious virus concentration within samples. In one system, virus-containing samples were subjected to serial 10-fold dilutions (typically, 10$^{-1}$ to 10$^{-6}$) in complete growth medium. Each dilution was then used to infect multiple wells of Huh-7.5 cells seeded in 96-well plates. Following 2 or 3 day incubation, the cells are fixed and subjected to immunohistochemical staining for NS5A expression, as above. The assay plate was then scored for the number of infected wells (i.e. at least one infected cell per well) for each dilution (FIG. 3) and the virus titer was then calculated as the 50% end-point tissue-culture infectious dose per ml (TCID$_{50}$/ml) according to the statistical method of Reed and Muench (Am. J. Hyg. 27:493-497 (1938)). The sensitivity of this assay was determined by volume of the lowest dilution and the number of replicates tested, and was typically 15.8 TCID$_{50}$s/ml.

The above assay was also used to determine the specific infectivity of full-length transcripts. Following RNA transfection, suspensions of the transfected cells were serially diluted (10$^{-1}$ to 10$^{-8}$) into a suspension of mock-transfected cells, which received no RNA. This allowed serial dilutions of the transfected cells to be examined without affecting the plating cell density. These dilutions were then plated onto 96 well plates as above, and incubated for two to four days. The conditioned media was removed to a new 96 well plate, subjected to two freeze-thaw cycles to ensure that viable cells were not transferred, and plated onto a 96 well plate previously seeded with naïve cells. The original 96 well plate and the infected 96 well plate were then stained for NS5A expression and the TCID$_{50}$ of transfection and infection were calculated as above.

Example 3

Growth of Virus

Figure 4:
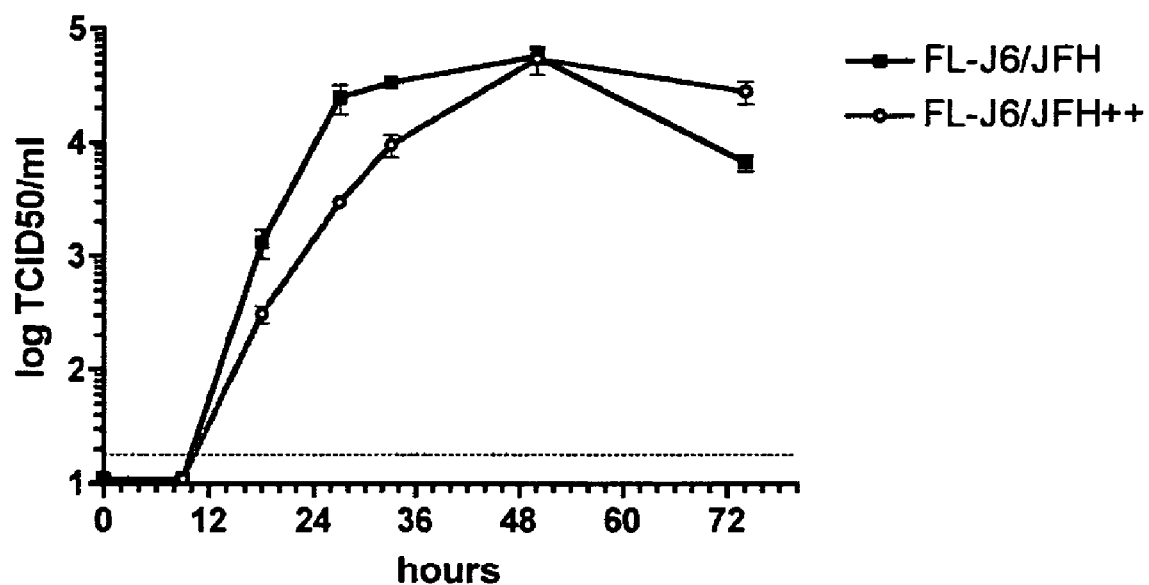
FIG. 4 demonstrates the growth of HCVcc. Following transfection of Huh-7.5 cells with FL-J6/JFH or FL-J6/JFH++ RNAs, cells were plated and incubated for the indicated times. For each time point, the conditioned media were harvested, clarified, and their titer determined as described in FIG. 3. Shown are the average±s.d. for four independent transfections of each genome. The dotted line indicates the limit of detection for these assays.

FIG. 4 shows a growth curve of FL-J6/JFH and FL-J6/JFH++ following electroporation of Huh-7.5 cells. Both viruses were efficiently released from cells following a 9-12 hour lag phase. Although the kinetics of FL-J6/JFH release were greater than that of FL-J6/JFH++, both viruses reached a peak of ≈5×10$^4$ TCID$_{50}$/ml between 48 and 72 hours post-electroporation.

Following this initial virus growth phase, virus was continuously produced by transfected cells. Therefore, cells can be passaged as normal and continued to produce virus. Since virus was detected in cells after 5 passages, virus cultures may be conveniently scaled up in this way.

Additionally, virus can be produced following infection of naïve cells. Typically, cells are infected at a multiplicity of infection (MOI) of less than one to minimize co-infection, washed, and fed with complete growth medium. Virus-containing supernatants are then collected over subsequent days, and infected cells may be further passaged.

Example 4

Virus Storage

Infectious HCVcc was efficiently secreted from infected cells, as conditioned medium contained ≈10-fold more infectivity than the lysates of infected cells. HCVcc preparations were therefore typically recovered as the conditioned media from infected cells. Conditioned media were clarified by centrifugation (3000×g for 10-30 minutes) to remove dead cells and debris, buffered with 20 mM Hepes (pH 7.4), and filtered (0.2 µm). Virus prepared in this way was stable for at least 6 weeks when stored at 4° C., protected from light. For longer term storage, HCVcc preparations can be dispensed into convenient aliquots and frozen at −80° C. Experiments have shown that the infectivity of HCV stored in this manner was unchanged for at least three rounds of freezing and thawing.

Example 5

Virus Concentration

For some purposes, it may be desirable to increase the titer of HCVcc. Infectious HCVcc particles were concentrated ≈30-fold by using Amicon Ultra 100,000 NMWCO ultrafiltration devices (Millipore), with recoveries of 70-100% of the input infectivity. In addition, infectious virus was efficiently precipitated with polyethylene glycol 8000 (PEG 8000). Virus preparations were mixed with ¼ volume 40% PEG 8000 in PBS, and chilled overnight at 4° C. Precipitated material was pelleted by centrifugation (8000×g for 10-30 minutes) and resuspended in a small volume of PBS or complete growth medium. Virus prepared in this way was concentrated more than 100-fold with a recovery of ≈50-100% of the input infectivity.

Example 6

Neutralization of HCVcc Entry

Figure 5:
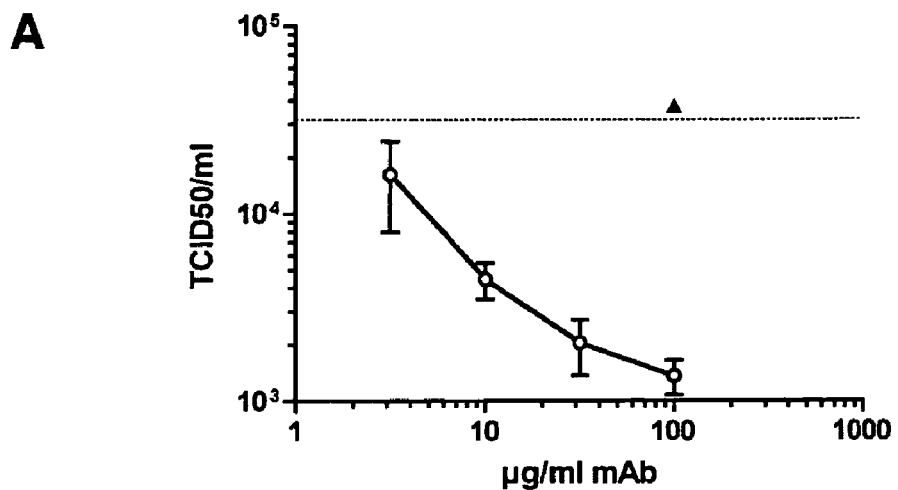
FIG. 5 demonstrates HCVcc neutralization and dependence on E2 and CD81. A) Independent samples of FL-J6/JFH++ ($3.16 \times 10^4$ TCID50/ml) were mixed with the indicated amounts of recombinant human monoclonal antibodies (IgG1) against HCV E2 (open circles) or dengue-3 E proteins (filled triangle). Following a 1 hour incubation at 37° C., the virus titers of each sample were determined as described for FIG. 3. Shown are the average±s.d. of three independent samples. The amount of input virus is indicated by the dashed line. B) Samples of FL-J6/JFH were incubated for 1 hour at 37° C. with 10 μg/ml of soluble recombinant CD81 or CD9 and used to infect naïve Huh-7.5. Infections were monitored at day 3 by immunostaining as described in FIG. 2B. C). FL-J6/JFH was used to infect standard HepG2 cells or HepG2 cells engineered to express human CD81. Infections were monitored as described in FIG. 2B.
Figure 5:
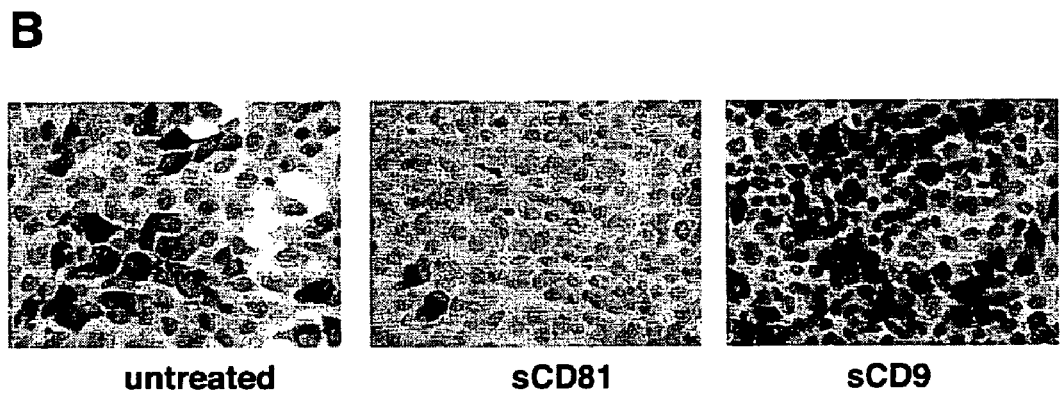
Figure 5:
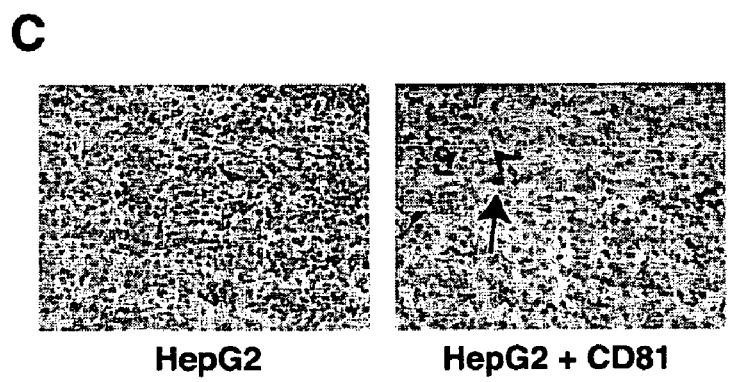

A human monoclonal antibody that specifically recognizes the HCV E2 glycoprotein decreased virus infectivity in a dose-dependent manner (FIG. 5A). This experiment demonstrated that HCVcc infectivity was dependent on the function of the E2 glycoprotein, and is the first direct observation of antibody neutralization for this virus.

Similarly, HCV-infected patient plasma were able to neutralize HCVcc infectivity. As most effective antiviral vaccines elicit strong neutralizing antibody responses, the described cell culture system will be useful in vaccine development in monitoring virus neutralization in a cell culture model.

To further examine the role of E2 in HCVcc entry, virus was preincubated with a recombinant form of the large extracellular loop from CD81, which binds E2 and acts as a receptor for HCV. This treatment blocked HCVcc infection, while the large extracellular loop of CD9 (a related tetraspanin) did not (FIG. 5B). In addition, the role of CD81 in mediating HCVcc entry was examined by infecting HepG2 cells, which lack CD81 expression, or HepG2 cells that have been engineered to express human CD81. As shown in FIG. 5C, only the CD81-expressing cells were infected with HCVcc. Taken together these data demonstrate that the viral E2 glycoprotein and the cellular CD81 receptor are critical determinants of HCVcc entry, and are promising targets for the design of HCV entry inhibitors.

Example 7

Characterization of HCVcc Virions

Figure 6:
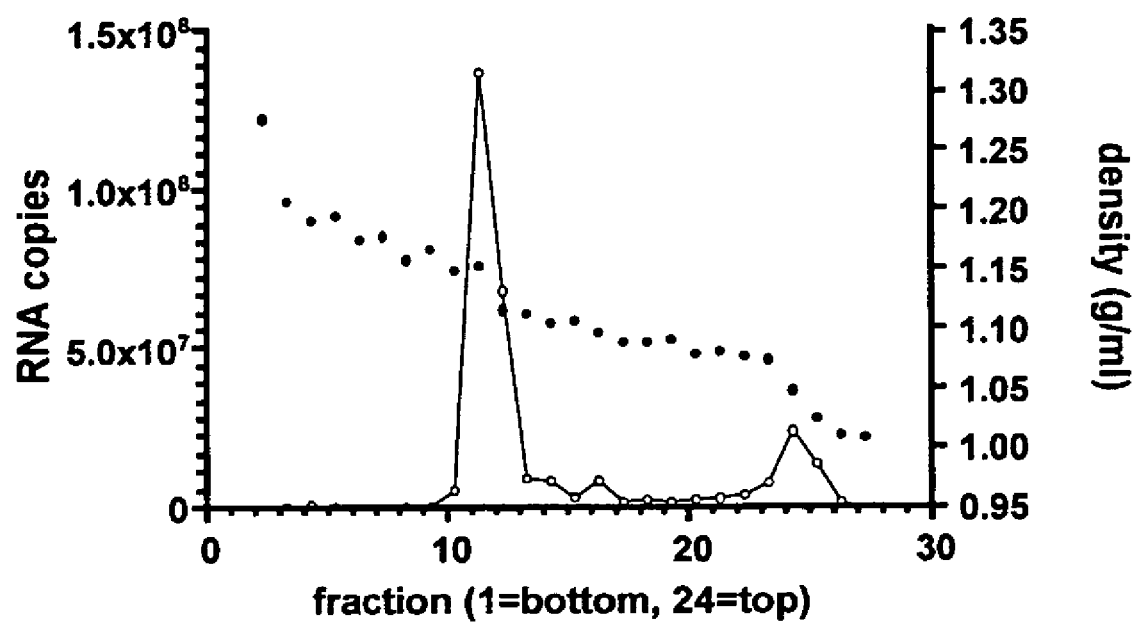
FIG. 6 demonstrates equilibrium banding of HCVcc by isopycnic centrifugation. 1 ml of FL-J6/JFH++ ($1 \times 10^5$ TCID50; $\approx 3 \times 10^8$ RNA molecules) was layed on top of a 10-40% iodixanol gradient and centrifuged for 6 hours at 274,000×g. 0.5 ml fractions were collected from the bottom of the gradient and analyzed for buoyant density (closed circles) and RNA quantity (open circles connected with a line).
Figure 7:
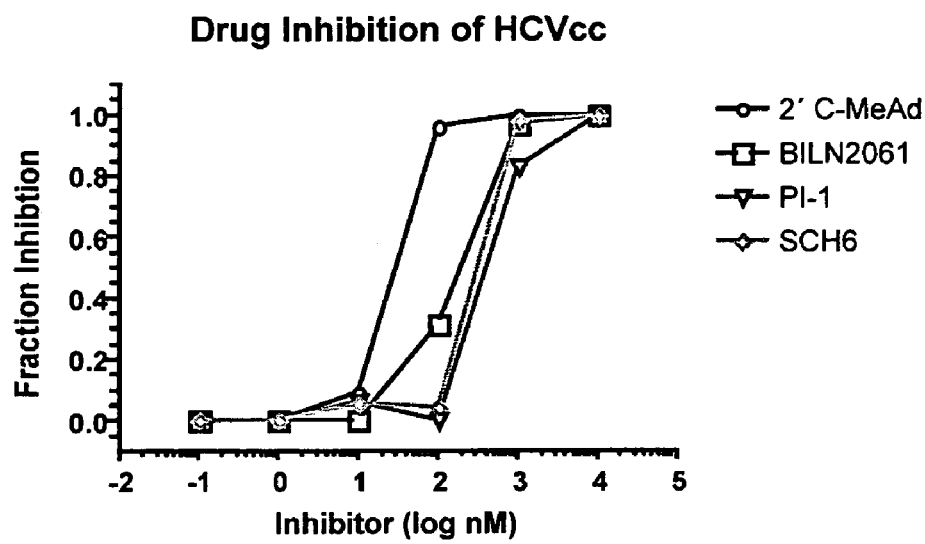
FIG. 7 demonstrates drug inhibition of HCVcc. Parallel cultures of Huh-7.5 cells were infected with FL-J6/JFH++ for 6 hours. Following removal of the inocula, cells were washed with PBS and fed with complete growth medium containing the indicated concentrations of antiviral drugs or a DMSO carrier control. RNAs were extracted after 2 days and the amount of accumulated HCVcc RNA quantitated by Taqman.

Conditions for the purification and characterization of infectious HCVcc particles was also examined. As shown in FIG. 6, a peak of FL-J6/JFH++ RNA was found to band at a buoyant density of 1.15 g/ml in an isopycnic 10-40% iodixanol gradient. This was intermediate between the buoyant densities of related viruses (flaviviruses, 1.21 g/ml; pestiviruses, 1.13 g/ml; (6)), and is consistent with other enveloped viruses. Nevertheless, a variety of particle densities have been reported for HCV in patient sera, with the most infectious material reportedly banding at <1.10 g/ml. This very low density may reflect the ability of HCV to interact with serum components, such as high- and low-density lipoproteins.

Example 8

Inhibitors of HCVcc Infection

A panel of experimental HCV antiviral compounds were examined for their ability to inhibit RNA replication at 48 hour post-infection with HCVcc. One of these compounds, 2'-C-methyladenosine (Merck) is a nucleoside analog that inhibits the HCV RNA polymerase. Three other compounds (PI-1, Vertex; BILN2061, Boerhinger Ingelheim; and SCH6, Schering-Plough) target the serine protease activity of NS3 by competitive binding. All of these compounds inhibited HCVcc replication, further confirming that this virus system is a useful and authentic model of HCV infection. Interestingly, the $IC_{50}$s that were observed for these drugs were somewhat different than those previously reported for HCV subgenomic replicons. For the polymerase inhibitor, the higher specific activity is likely due to the fact that we measured the accumulation of nascent RNAs post-infection, whereas replicon-based assays examine the decay of RNA after inhibiting established replication. The reduced activities of the protease inhibitors likely reflect reduced affinities of these drugs, developed to genotype 1 proteases, to bind to the JFH NS3 protein. These data demonstrate the utility of the cell culture system described herein in developing antiviral drugs that target HCV.

Example 9

Development of High Throughput Reporters of HCVcc Replication and Entry

Figure 8:
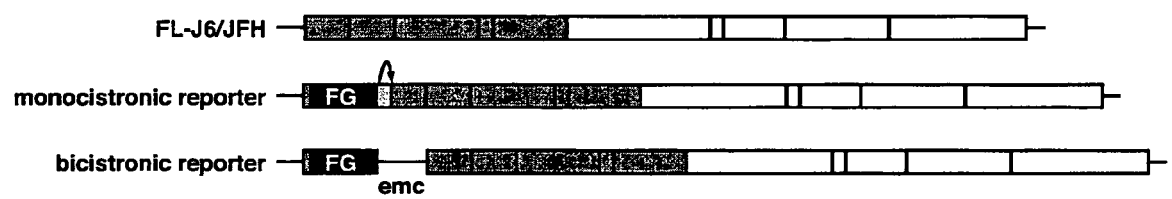
FIG. 8 demonstrates reporter gene expression by HCVcc. A) The design of monocistronic and bicistronic genomes to express foreign genes (FG). B) Expression of *Renilla* luciferase after infection with a monocistronic HCVcc reporter virus. Conditioned media from cells transfected with a monocistronic HCVcc reporter (wt) or replication-defective control (GND) were harvested at 24 and 48 hours post transfection and used to infect naïve Huh-7.5 cells. Infected cells were lysed at 48 hours and the amount of luciferase activity was determined by using a standard assay (Promega). Mock refers to naïve cells that did not receive conditioned media.
Figure 8:
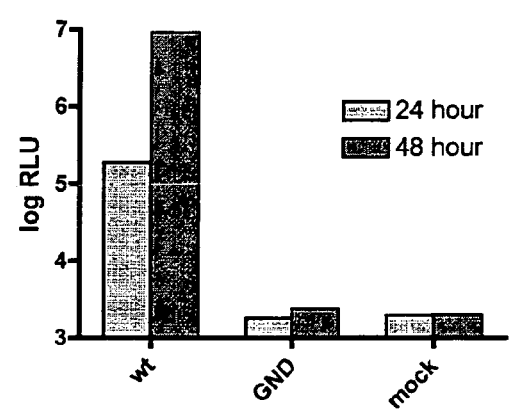

The HCVcc infection system has wide application in drug development. Since replication assays based on immunohistochemical staining and/or RNA measurements can be cumbersome, versions of the HCVcc system with reporter genes was undertaken. In one configuration, the monocistronic design, a foreign gene was fused to the N-terminal coding region of the core gene, followed by a small cassette that mediated proteolysis at its own C-terminus, followed by the complete core-NS5B coding region (FIG. 8A). FIG. 8B demonstrates that a widely used reporter gene, *Renilla* luciferase, can be expressed in naïve Huh-7.5 cells following infection with the monocistronic virus. Similarly, green fluorescent protein was expressed via a monocistronic FL-J6/JFH (not shown). In addition, bicistronic HCVcc genomes have been constructed. These derivatives utilize an internal ribosome entry site such as from encephalomyocarditis virus, to drive expression of the HCV polyprotein (FIG. 8B). Following infection of naïve cells with a bicistronic HCVcc that expresses the neomycin resistance gene (GPTII), G418-resistant cells can be selected (not shown).

Example 10

Improved Methods for Culturing HCV

It was of interest to ascertain culturing conditions that increase the titer of infectious HCVcc. A large number of cell culture conditions were tested for their effect on HCVcc production. These included the choice of cell culture media, amount and type of fetal calf serum, as well as the addition of various additive compounds. One compound, N-acetylcysteine consistently gave higher levels of HCVcc as determined by $TCID_{50}$ assay. For example, the following titers were recorded: $3.10 \times 10^6$ $TCID_{50}$ (25 mM N-acetylcysteine) vs. $1.06 \times 10^6$ $TCID_{50}$ (5 mM N-acetylcysteine) vs. $2.65 \times 10^5$ $TCID_{50}$ (no N-acetylcysteine). Thus, the use of this compound in HCV-containing cell cultures permits a significant increase in yield of infectious HCVcc. Conditions have also been established for serum-free propagation of Huh-7.5 cells and HCVcc infection and production. These conditions include, but are not limited to, Dulbecco's Modified Eagle's Medium (DMEM)/F12 medium containing 10 μg/ml transferrin, 2 μg/ml insulin, 7.6 μM free fatty acids, 0.3 μM selenium, 0.1 μM hydrocortisone, 0.20% bovine serum albumin, and 20 ng/ml epidermal growth factor.

Example 11

Methods to Select For HCV Variants With Improved Growth Properties

We have developed a method to select for HCVcc variants that spread more efficiently in culture. This approach starts with HCV genomes that efficiently replicate intracellularly (RNA replication), but produce moderate to undetectable levels of infectious virus particles. Since HCV RNA replication is extremely error prone, mutations will naturally accumulate over time within a population of progeny genomes maintained in culture. Mutations that are detrimental to the viral life cycle should be lost during subsequent rounds of replication. However mutations that enhance some aspect of the viral life cycle, such as infectious virus production, will have a selective advantage and should therefore spread through the culture.

A co-culturing approach was undertaken to select for HCV variants with enhanced capacity to produce infectious virus. Under normal conditions, only a subset (≈30%) of cells are productively transfected with HCV genomes, as detected by NS5A-positive staining at 48 hour post-transfection. More than 95% of cells are positive for NS5A staining by 96 hour post-transfection with an HCV genome that produces infectious virus, such as FL-J6/JFH. This increase in NS5A-positive cells is consistent with the spread of infectious HCVcc through the culture. On the other hand, cultures transfected with RNAs that do not produce infectious virus remain ≦30% NS5A-positive at 96 hour post-transfection due to the lack of virus spread. Upon passage of cells that do not produce infectious virus, the percentage of NS5A-positive cells progressively drops to <1%, likely due to a growth disadvantage of cells harboring the viral RNA. However a substantially higher proportion of NS5A-positive cells will be maintained within the culture if mutations allowing virus production arise within the population of replicating HCV RNAs. This increase in NS5A-positive cells will again be due to spread of infectious HCVcc through the culture, although such selected cultures typically contain <95% NS5A-positive cells. This may be due to the use of non-optimal growth conditions or to the lack of permissiveness within a proportion of the cells. This method can be extended to select for functional HCVcc variants for any HCV genotype, subtype or isolate as demonstrated by the following example.

Example 12

Constructing Functional Chimeras for Other HCV Genotypes

Figure 9:
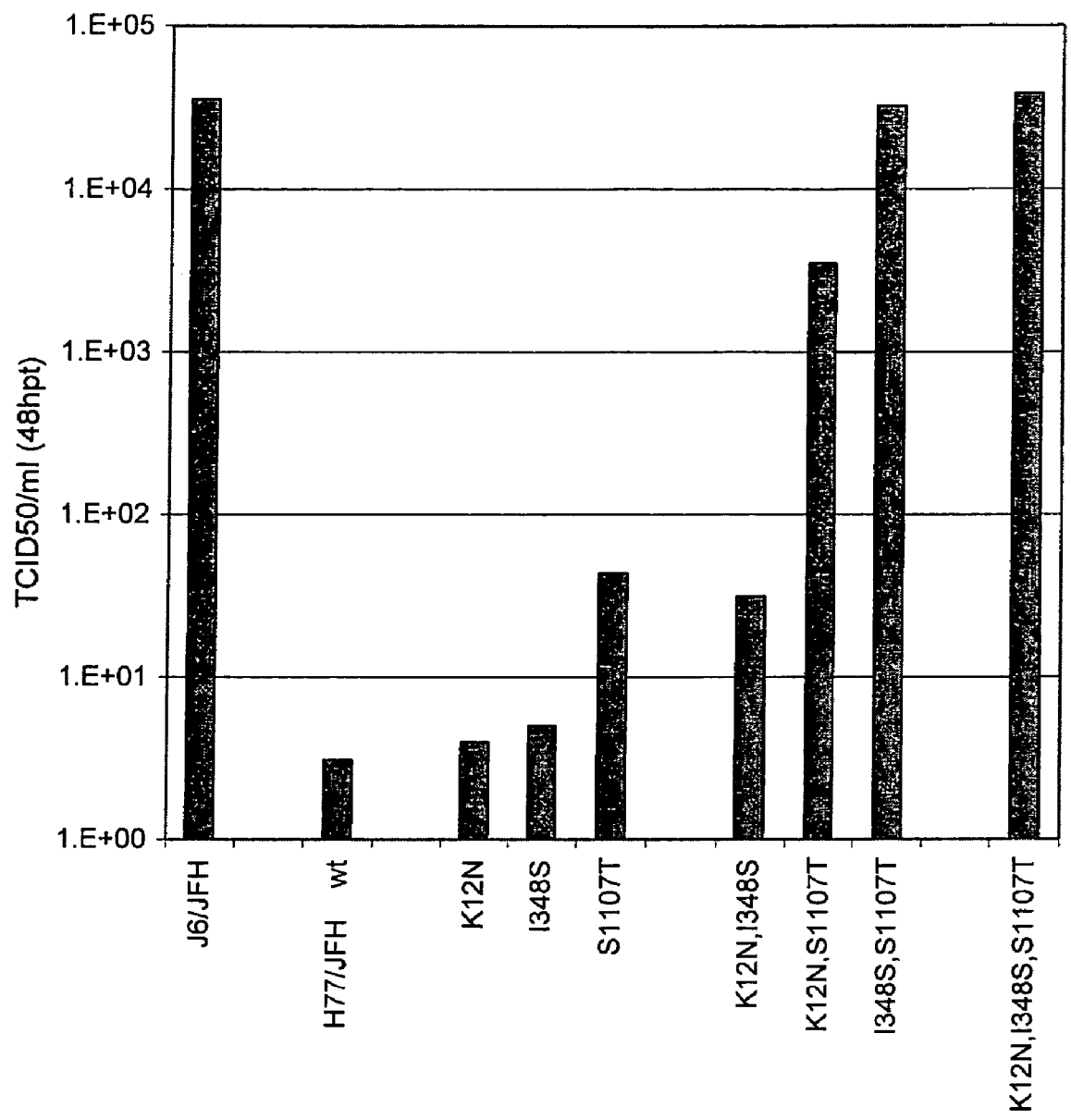
FIG. 9. Effects of mutations on H77/JFH infectious virus production. Supernatants from cells were transfected with J6/JFH (first bar) or H77/JFH variants with no additional mutations (second bar) or with combinations of identified mutations that enhance virus release, were collected 48 hours post transfection. The amounts of infectious virus present in these supernatants was calculated by TCID50 assay, as reported.

The above method was used to identify mutations that allow a chimeric genotype 2a JFH-1 HCV RNA encoding the core-NS2 region from the genotype 1a H77 isolate to efficiently produce infectious virus (SEQ ID NO:2). This chimeric RNA exhibited the identical RNA replication characteristics as the FL-J6/JFH chimera, but failed to secrete detectable levels of infectious virus into the supernatants of transfected cell cultures. While subsequent passage of transfected cell cultures most frequently resulted in eventual loss of detectable viral species, likely through dilution as described above, a few NS5A-positive cells were maintained following extensive passaging of some cultures. Supernatants from these cultures were found to contain significant amounts of infectious virus, which were amplified through several rounds of infecting naïve cells. HCV-specific cDNAs were constructed from RNA present in infected cells by RT-PCR. Sequencing of these cDNAs revealed the presence of mutations that, when reengineered into the chimeric FL-H77/JFH genome, resulted in RNAs that produced high levels of infectious virus (SEQ ID NO: 3). The amino acid substitutions responsible for this phenotype, numbered according to their codon within the FL-H77/JFH polyprotein, were found within core (K12N) (SEQ ID NO:3), E1 (I348S) (SEQ ID NO:4), and NS3 (S1107T) (SEQ ID NO:5). While none of these mutations had a large effect on virus production alone (15-100 $TCID_{50}$/ml vs. <15 $TCID_{50}$/ml for the wild type FL-H77/JFH), combinations of two or three of these mutations resulted in dramatic increases in the level of virus release post transfection (up to $1 \times 10^5$ $TCID_{50}$/ml). Such an approach has also been utilized to isolate a mutation in E1 (A269T) that enhances the ability of a JFH-1 chimera encoding J6 core-p7 and H77 NS2 to produce infectious virus following transfection (from ~100 $TCID_{50}$/ml for the parental RNA to >$1 \times 10^5$ $TCID_{50}$/ml for the mutant) (FIG. 9).

Example 13

Construction of HCV Genomes Encoding Reporter Genes Suitable for Use in Applications Including, but not Limited to, the Screening of Compounds with Potential Antiviral Activity In another monocistronic configuration, a reporter gene of interest is fused to the C-terminus of p7. To liberate the reporter protein from the HCV polyprotein, the p7/NS2 signal peptidase cleavage site is included at the N-terminus of the reporter protein, while a small cassette (e.g. the EMCV 2A peptide coding sequence), which mediates its own cleavage from the N-terminus of the NS2 protein, is fused to the C-terminus of the reporter protein. Using this alternative monocistronic configuration, HCV genomes have been constructed that encode the widely used reporter genes green fluorescent protein and *Renilla* luciferase. Such genomes replicate in cell culture and produce HCVcc.

In an effort to further simplify the development of high-throughput antiviral drug screening protocols, HCV genomes have been constructed (using the monocistronic and/or bicistronic genome configurations described above) that encode reporter proteins that are secreted into the cell culture supernatant. Examples of such secreted reporter proteins include secreted alkaline phosphatase (SEAP) and Gaussia luciferase. Permissive naïve cells that are either transfected or infected with such viral genomes result in the expression and subsequent secretion of said reporter proteins into the cell culture supernatant. A quantitative measure of reporter protein activity can then be obtained using cell culture supernatants directly without the need for generating cellular extracts as is necessary for such non-secreted reporter proteins as *Renilla* luciferase (described above). The approach can be used to construct reporter HCVcc derivatives encoding convenient reporter genes, dominant selectable markers, or tags for purifying large quantities of virus for structural studies or vaccine applications.

Example 14

Methods to Screen for JFH-1 Like Isolates

FL-J6/JFH-derived HCVcc is infectious in vivo, as demonstrated herein, and viruses recovered from these animals retain their infectivity in cell culture. These results formally demonstrate that it is possible to recover infectious HCV in cell culture from animal tissues, and that the system for producing HCVcc described herein can be used as a positive control to screen for additional isolates of HCV that replicate and produce infectious virus in cell culture. A screening system would consist of a cell line, such as a derivative of Huh-7 or Huh-7.5, which responds to productive HCVcc infection by expression of a reporter gene such as GFP or a dominant selectable marker such as GPTII. Said cell lines would then be used to screen clinical samples to identify HCV isolates capable of infection and spread within cell culture. The method of producing HCVcc can be used to verify this cell culture-based screening system.

What is claimed is:

1. An isolated nucleic acid comprising a chimeric Hepatitis C Virus (HCV) genome, wherein said chimeric HCV genome comprises the structural core, E1 and E2 genes and nonstructural p7 and NS2 genes from HCV strain H77 a 5' non-coding region (NCR), nonstructural NS3, NS4A, NS4B, NS5A, NS5B genes and a 3' non-coding region (NCR) from HCV strain JFH-1, wherein said chimeric HCV genome comprises at least one mutation selected for enhanced capacity to produce infectious virus, and wherein said chimeric HCV genome is infectious.

2. The isolated nucleic acid molecule of claim 1, wherein said nucleic acid comprises a sequence sharing at least 90% identity with that set forth in SEQ ID NO: 2 and/or 3 and/or 4 and/or 5.

3. The isolated nucleic acid molecule of claim 1, wherein said nucleic acid encodes an H2476L mutation in the NS5B protein, a S1107T mutation in the NS3 protein, a K12N mutation in the core protein, an I348S mutation or an A269T mutation in the E1 protein, or combinations thereof.

4. The isolated nucleic acid molecule of claim 1, wherein said nucleic acid further comprises a reporter gene, a dominant selectable marker, or a tag for purification.

5. The isolated nucleic acid molecule of claim 4, wherein said reporter gene encodes *Renilla* luciferase, secreted alkaline phosphatase (SEAP), Gaussia luciferase or the green fluorescent protein.

6. The isolated nucleic acid molecule of claim 4, wherein said dominant selectable marker encodes a neomycin phosphotransferase.

7. A non-human animal or vector comprising the isolated nucleic acid molecule of claim 1.

8. An isolated cell comprising the vector of claim 7.

9. The cell of claim 8, wherein said cell is of the Huh-7 or Huh-7.5 cell line.

10. The cell of claim 8, wherein said cell is cultured in a media comprising N-acetylcysteine, at a concentration of at least about 5 mM.

11. A method for producing infectious HCV, comprising contacting a cell with an isolated nucleic acid comprising a chimeric HCV genome, wherein said chimeric HCV genome comprises the structural core, E1 and E2 genes and nonstructural p7 and NS2 genes from HCV strain H77, a 5' non-coding region (NCR), nonstructural NS3, NS4A, NS4B, NS5A, NS5B genes and a 3' non-coding region (NCR) from HCV strain JFH-1, wherein said chimeric HCV genome comprises at least one mutation selected for enhanced capacity to produce infectious virus, and wherein said chimeric HCV genome is infectious.

12. The method of claim 11, wherein said nucleic acid comprises a sequence sharing at least 90% identity with that set forth in SEQ ID NO: 2 and/or 3 and/or 4 and/or 5.

13. The method of claim 11, wherein said nucleic acid encodes an H2476L mutation in the NS5B protein, a S1107T mutation in the NS3 protein, a K12N mutation in the core protein, an I348S mutation or an A269T mutation in the E1 protein, or combinations thereof.

14. The method of claim 11, wherein said cell is cultured in a media comprising N-acetylcysteine, at a concentration of about at least 5 mM.

15. The method of claim 11, wherein said infectious HCV is produced at a titer of $10^1$-$10^6$ TCID50/ml (50% end-point tissue-culture infectious dose per ml).

16. A viral particle comprising a chimeric Hepatitis C Virus (HCV) genome, wherein said chimeric HCV genome comprises the structural core, E1 and E2 genes and nonstructural p7 and NS2 genes from a first HCV strain, a 5' non-coding region (NCR), nonstructural NS3, NS4A, NS4B, NS5A, NS5B genes and a 3' non-coding region (NCR) from a second HCV strain, wherein said first HCV is a J6 strain, wherein said second HCV strain is strain JFH-1, and wherein said viral particle is infectious HCV.

17. The infectious HCV of claim 16, wherein said infectious HCV is at a titer of $10^1$-$10^6$ TCID50/ml (50% end-point tissue-culture infectious dose per ml).

18. An isolated nucleic acid comprising a chimeric Hepatitis C Virus (HCV) genome, wherein said chimeric HCV genome comprises the structural core, E1 and E2 genes and nonstructural p7 and NS2 genes from HCV strain J6, a 5' non-coding region (NCR), nonstructural NS3, NS4A, NS4B, NS5A, NS5B genes and a 3' non-coding region (NCR) from HCV strain JFH-1, and wherein said chimeric HCV genome is infectious.

19. The isolated nucleic acid molecule of claim 18, wherein said nucleic acid comprises a sequence sharing at least 90% identity with that set forth in SEQ ID NO: 1.

20. The isolated nucleic acid molecule of claim 18, wherein said nucleic acid further comprises a reporter gene, a dominant selectable marker, or a tag for purification.

21. The isolated nucleic acid molecule of claim 20, wherein said reporter gene encodes *Renilla* luciferase, secreted alkaline phosphatase (SEAP), Gaussia luciferase or the green fluorescent protein.

22. The isolated nucleic acid molecule of claim 18, wherein said dominant selectable marker encodes a neomycin phosphotransferase.

23. A non-human animal or vector comprising the isolated nucleic acid molecule of claim 18.

24. An isolated cell comprising the vector of claim 23.

25. The cell of claim 24, wherein said cell is of the Huh-7 or Huh-7.5 cell line.

26. The cell of claim 25, wherein said cell is cultured in a media comprising N-acetylcysteine, at a concentration of at least about 5 mM.

27. A method for producing infectious HCV, comprising contacting a cell with an isolated nucleic acid comprising a chimeric HCV genome, wherein said chimeric HCV genome comprises the structural core, E1 and E2 genes and nonstructural p7 and NS2 genes from HCV strain J6, a 5' non-coding region (NCR), nonstructural NS3, NS4A, NS4B, NS5A, NS5B genes and a 3' non-coding region (NCR) from HCV strain JFH-1, and wherein said chimeric HCV genome is infectious.

28. The method of claim 27, wherein said nucleic acid comprises a sequence sharing at least 90% identity with that set forth in SEQ ID NO: 1.

29. The method of claim 27, wherein said cell is cultured in a media comprising N-acetylcysteine, at a concentration of about at least 5 mM.

30. A viral particle comprising a chimeric Hepatitis C Virus (HCV) genome, wherein said chimeric HCV genome comprises the structural core, E1 and E2 genes and nonstructural p7 and NS2 genes from a first HCV strain, a 5' non-coding region (NCR), nonstructural NS3, NS4A, NS4B, NS5A, NS5B genes and a 3' non-coding region (NCR) from a second HCV strain, wherein said first HCV is an H77 HCV strain, wherein said second HCV strain is strain JFH-1, wherein said chimeric HCV genome comprises at least one mutation selected for enhanced capacity to produce infectious virus, and wherein said viral particle is infectious HCV.

31. The viral particle of claim 30, wherein said chimeric HCV genome encodes an H2476L mutation in the NS5B protein, a S1107T mutation in the NS3 protein, a K12N mutation in the core protein, an I348S mutation or an A269T mutation in the E1 protein, or combinations thereof.

* * * * *

UNITED STATES PATENT AND TRADEMARK OFFICE
CERTIFICATE OF CORRECTION

PATENT NO. : 7,674,612 B2 Page 1 of 1
APPLICATION NO. : 11/366839
DATED : March 9, 2010
INVENTOR(S) : Charles Rice et al.

It is certified that error appears in the above-identified patent and that said Letters Patent is hereby corrected as shown below:

In Column 1, the sentence reading "The government may have certain rights in the invention." that spans lines 16-17 should read --The government has certain rights in the invention.--.

Signed and Sealed this

First Day of June, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 9675
<212> TYPE: DNA
<213> ORGANISM: Hepatitis C virus

<400> SEQUENCE: 1

```
acctgcccct aatagggcg acactccgcc atgaatcact ccctgtgag gaactactgt      60
cttcacgcag aaagcgccta gccatggcgt tagtatgagt gtcgtacagc ctccaggccc     120
cccctcccg ggagagccat agtggtctgc ggaaccggtg agtacaccgg aattgccggg     180
aagactgggt cctttcttgg ataaacccac tctatgcccg ccatttggg cgtgcccccg     240
caagactgct agccgagtag cgttgggttg cgaaaggcct tgtggtactg cctgataggg     300
cgcttgcgag tgccccggga ggtctcgtag accgtgcacc atgagcacaa atcctaaacc     360
tcaaagaaaa accaaaagaa acaccaaccg tcgcccacaa gacgttaagt tccgggcgg     420
cggccagatc gttggcggag tatacttgtt gccgcgcagg ggcccaggt tgggtgtgcg     480
cgcgacaagg aagacttcgg agcggtccca gccacgtgga aggcgccagc ccatccctaa     540
agatcggcgc tccactggca aatcctgggg aaaaccagga taccctggc ccctatacgg     600
gaatgaggga ctcggctggg caggatggct cctgtccccc cgaggttccc gtccctcttg     660
gggccccaat gaccccggc ataggtcgcg caacgtgggt aaggtcatcg ataccctaac     720
gtgcggcttt gccgacctca tggggtacat ccctgtcgtg ggcgccccgc tcggcggcgt     780
cgccagagct ctcgcgcatg gcgtgagagt cctggaggac ggggttaatt ttgcaacagg     840
gaacttaccc ggttgctcct tttctatctt cttgctggcc ctgctgtcct gcatcaccac     900
cccggtctcc gctgccgaag tgaagaacat cagtaccggc tacatggtga ctaacgactg     960
caccaatgac agcattacct ggcagctcca ggctgctgtc ctccacgtcc ccgggtgcgt    1020
cccgtgcgag aaagtgggga atgcatctca gtgctggata ccggtctcac cgaatgtggc    1080
cgtgcagcgg cccggcgccc tcacgcaggg cttgcgacg cacatcgaca tggttgtgat    1140
gtccgccacg ctctgctctg ccctctacgt gggggacctc tgcggtgggg tgatgctcgc    1200
agcccaaatg ttcattgtct cgccgcagca ccactggttt gtccaagact gcaattgctc    1260
catctaccct ggtaccatca ctggacaccg catggcatgg gacatgatga tgaactggtc    1320
gcccacggct accatgatct ggcgtacgc gatgcgtgtc cccgaggtca ttatagacat    1380
cattagcggg gctcattggg gcgtcatgtt cggcttggcc tacttctcta tgcagggagc    1440
gtgggcgaaa gtcgttgtca tccttctgtt ggccgccggg gtgacgcgc gcacccatac    1500
tgttgggggt tctgccgcgc agaccaccgg gcgcctcacc agcttatttg acatgggccc    1560
caggcagaaa atccagctcg ttaacaccaa tggcagctgg cacatcaacc gcaccgccct    1620
gaactgcaat gactccttgc acaccggctt tatcgcgtct ctgttctaca cccacagctt    1680
caactcgtca ggatgtcccg aacgcatgtc cgcctgccgc agtatcgagg ccttccgggt    1740
gggatgggc gccttgcaat atgaggataa tgtcaccaat ccagaggata tgagaccta    1800
ttgctggcac tacccaccaa ggcagtgtgg cgtggtctcc gcgaagactg tgtgtggccc    1860
```

```
agtgtactgt tcaccccca gcccagtggt agtgggcacg accgacaggc ttggagcgcc    1920
cacttacacg tgggggagaa atgagacaga tgtcttccta ttgaacagca ctcgaccacc    1980
gctggggtca tggttcggct gcacgtggat gaactcttct ggctacacca agacttgcgg    2040
cgcaccaccc tgccgtacta gagctgactt caacgccagc acggacctgt tgtgcccccac   2100 ggactgtttt aggaagcatc ctgataccac ttacctcaaa tgcggctctg ggccctggct    2160
cacgccaagg tgcctgatcg actaccccta caggctctgg cattaccect gcacagttaa    2220 ctataccatc ttcaaaataa ggatgtatgt gggaggggtt gagcacaggc tcacggctgc    2280
atgcaatttc actcgtgggg atcgttcaa cttggaggac agagacagaa gtcaactgtc     2340
tcctttgttg cactccacca cggaatgggc cattttacct tgctcttact cggacctgcc    2400
cgccttgtcg actggtcttc tccacctcca ccaaaacatc gtggacgtac aattcatgta    2460
tggcctatca cctgccctca caaaatacat cgtccgatgg gagtgggtaa tactcttatt    2520
cctgctctta gcgacgcca gggtttgcgc ctgcttatgg atgctcatct tgtttgggcca    2580 ggccgaagca gcactagaga agctggtcat cttgcacgct gcgagcgcag ctagctgcaa    2640
tggcttccta tattttgtca tcttttttcgt ggctgcttgg tacatcaagg gtcgggtagt   2700 cccccttagct acctattccc tcactggcct gtggtccttt agcctactgc tcctagcatt   2760
gccccaacag gcttatgctt atgacgcatc tgtgcatggc cagataggag cggctctgct    2820
ggtaatgatc actctcttta ctctcacccc cgggtataag acccttctca gccggttttt    2880
gtggtggttg tgctatcttc tgaccctggg ggaagctatg gtccaggagt gggcaccacc    2940
tatgcaggtg cgcggtggcc gtgatggcat catatgggcc gtcgccatat tctacccagg    3000
tgtggtgttt gacataacca agtggctctt ggcggtgctt gggcctgctt acctcctaaa    3060
aggtgctttg acgcgcgtgc cgtacttcgt cagggctcac gctctactga ggatgtgcac    3120
catggcaagg catctcgcgg ggggcaggta cgtccagatg gcgctactag cccttggcag    3180
gtggactggc acttacatct atgaccacct caccccctatg tcggattggg ctgctagtgg   3240
cctgcgggac ctggcggtcg ccgttgagcc tatcatcttc agtccgatgg agaagaaagt    3300
cattgtctgg ggagcggaga cagctgcttg tggggacatt ttacacggac ttcccgtgtc    3360
cgcccgactt ggtcgggagg tcctccttgg cccagctgat ggctataccct ccaaggggtg   3420 gagtcttctc gctcccatca ctgcttatgc ccagcaaaca cgaggcctcc tgggcgccat    3480
agtggtgagt atgacggggc gtgacaggac agaacaggcc ggggaagtcc aaatcctgtc    3540
cacagtctct cagtccttcc tcggaacaac catctcgggg gttttgtgga ctgtttacca    3600
cggagctggc aacaagactc tagccggctt acggggtccg gtcacgcaga tgtactcgag    3660
tgctgagggg gacttggtag ctggcccag ccccccctggg accaagtctt tggagccgtg     3720
caagtgtgga gccgtcgacc tatatctggt cacgcggaac gctgatgtca tccccggctcg   3780 gagacgcggg gacaagcggg gagcattgct ctccccgaga cccatttcga ccttgaaggg    3840
gtcctcgggg gggccggtgc tctgccctag gggccacgtc gttgggctct tccgagcagc    3900
tgtgtgctct cggggcgtgg ccaaatccat cgatttcatc cccgttgaga cactcgacgt    3960
tgttacaagg tctcccactt tcagtgacaa cagcacgcca ccggctgtgc cccagaccta    4020
tcaggtcggg tacttgcatg ctccaactgg cagtggaaag agcaccaagg tccctgtcgc    4080
gtatgccgcc caggggtaca agtactagt gcttaacccc tcggtagctg ccaccctggg    4140
gtttggggcg tacctatcca aggcacatgg catcaatccc aacattagga ctggagtcag    4200
gccgtgatga ccggggaggc catcacgtac tccacatatg gcaaatttct cgccgatggg    4260
```

-continued

```
ggctgcgcta gcggcgccta tgacatcatc atatgcgatg aatgccacgc tgtggatgct    4320
acctccattc tcggcatcgg aacggtcctt gatcaagcag agacagccgg ggtcagacta    4380
actgtgctgg ctacgccac accccccggg tcagtgacaa ccccccatcc cgatatagaa     4440
gaggtaggcc tcgggcggga gggtgagatc cccttctatg ggagggcgat tccctatcc     4500 tgcatcaagg gagggagaca cctgattttc tgccactcaa agaaaaagtg tgacgagctc    4560
gcggcggccc ttcggggcat gggcttgaat gccgtggcat actatagagg gttggacgtc    4620
tccataatac cagctcaggg agatgtggtg gtcgtcgcca ccgacgccct catgacgggg    4680
tacactggag actttgactc cgtgatcgac tgcaatgtag cggtcaccca agctgtcgac    4740
ttcagcctgg accccacctt cactataacc acacagactg tcccacaaga cgctgtctca    4800
cgcagtcagc gccgcgggcg cacaggtaga ggaagacagg gcacttatag gtatgtttcc    4860
actggtgaac gagcctcagg aatgtttgac agtgtagtgc tttgtgagtg ctacgacgca    4920
ggggctgcgt ggtacgatct cacaccagcg gagaccaccg tcaggcttag agcgtatttc    4980
aacacgcccg gcctacccgt gtgtcaagac catcttgaat tttgggaggc agttttcacc    5040
ggcctcacac acatagacgc ccacttcctc tcccaaacaa agcaagcggg ggagaacttc    5100
gcgtacctag tagcctacca agctacggtg tgcgccagag ccaaggcccc tccccgtcc    5160 tgggacgcca tgtggaagtg cctggcccga ctcaagccta cgcttgcggg ccccacacct    5220
ctcctgtacc gtttgggccc tattaccaat gaggtcaccc tcacacaccc tgggacgaag    5280
tacatcgcca catgcatgca agctgacctt gaggtcatga ccagcacgtg ggtcctagct    5340
ggaggagtcc tggcagccgt cgccgcatat tgcctggcga ctggatgcgt ttccatcatc    5400
ggccgcttgc acgtcaacca gcgagtcgtc gttgcgccgg ataaggaggt cctgtatgag    5460
gcttttgatg agatggagga atgcgcctct agggcggctc tcatcgaaga ggggcagcgg    5520
atagccgaga tgttgaagtc caagatccaa ggcttgctgc agcaggcctc taagcaggcc    5580
caggacatac aacccgctat gcaggcttca tggcccaaag tggaacaatt ttgggccaga    5640
cacatgtgga acttcattag cggcatccaa tacctcgcag gattgtcaac actgccaggg    5700
aaccccgcgg tggcttccat gatggcattc agtgccgccc tcaccagtcc gttgtcgacc    5760
agtaccacca tccttctcaa catcatggga ggctggttag cgtcccagat cgcaccaccc    5820 gcggggggcca ccggctttgt cgtcagtggc ctggtggggg ctgccgtggg cagcataggc    5880
ctgggtaagg tgctggtgga catcctggca ggatatggtg cgggcatttc gggggccctc    5940
gtcgcattca agatcatgtc tggcgagaag ccctctatgg aagatgtcat caatctactg    6000
cctgggatcc tgtctccggg agccctggtg gtggggtca tctgcgcggc cattctgcgc    6060
cgccacgtgg gaccggggga gggcgcggtc caatggatga acaggcttat tgcctttgct    6120
tccagaggaa accacgtcgc ccctactcac tacgtgacgg agtcggatgc gtcgcagcgt    6180
gtgacccaac tacttggctc tcttactata accagcctac tcagaagact ccacaattgg    6240
ataactgagg actgccccat ccatgctcc ggatcctggc tccgcgacgt gtgggactgg    6300
gtttgcacca tcttgacaga cttcaaaaat tggctgacct ctaaattgtt ccccaagctg    6360
cccggcctcc ccttcatcct tgtcaaaagg ggtacaaggg tgtgtgggcc ggcactggca    6420
tcatgaccac gcgctgccct tgcggcgcca acatctctgg caatgtccgc ctgggctcta    6480
tgaggatcac agggcctaaa acctgcatga acacctggca ggggaccttt cctatcaatt    6540
gctacacgga gggccagtgc gcgccgaaac cccccacgaa ctacaagacc gccatctgga    6600
```

```
gggtggcggc ctcggagtac gcggaggtga cgcagcatgg gtcgtactcc tatgtaacag   6660
gactgaccac tgacaatctg aaaattcctt gccaactacc ttctccagag ttttctcct   6720 gggtggacgg tgtgcagatc cataggtttg cacccacacc aaagccgttt ttccgggatg   6780
aggtctcgtt ctgcgttggg cttaattcct atgctgtcgg gtcccagctt ccctgtgaac   6840
ctgagcccga cgcagacgta ttgaggtcca tgctaacaga tccgcccac atcacggcgg    6900 agactgcggc gcggcgcttg gcacggggat cacctccatc tgaggcgagc tcctcagtga   6960
gccagctatc agcaccgtcg ctgcgggcca cctgcaccac ccacagcaac acctatgacg   7020
tggacatggt cgatgccaac ctgctcatgg agggcggtgt ggctcagaca gagcctgagt   7080
ccagggtgcc cgttctggac tttctcgagc caatggccga ggaagagagc gaccttgagc   7140
cctcaaacca tcggagtgca tgctccccag gagcgggttt ccacgggcct taccggcttg   7200
ggcacggcct gactacaacc cgccgctcgt ggaatcgtgg aggaggccag attaccaacc   7260
gcccaccgtt gctggttgtg ctctcccccc ccccaagaag gccccgacgc ctcccccaag   7320
gagacgccgg acagtgggtc tgagcgagag caccatatca gaagccctcc agcaactggc   7380
catcaagacc tttggccagc cccctcgag cggtgatgca ggctcgtcca cggggcggg    7440 cgccgccgaa tccggcggtc cgacgtcccc tggtgagccg gcccctcag agacaggttc    7500 cgcctcctct atgccccccc tcaggggga gcctggagat ccggacctgg agtctgatca    7560
ggtagagctt caacctcccc cccaggggg gggggtagct cccggttcgg gctcggggtc    7620
ttggtctact tgctccgagg aggacgatac caccgtgtgc tgctccatgt catactcctg   7680
gaccggggct ctaataactc cctgtagccc cgaagaggaa aagttgccaa tcaacccttt   7740
gagtaactcg ctgttgcgat accataacaa ggtgtactgt acaacatcaa agagcgcctc   7800
acagagggct aaaaaggtaa cttttgacag gacgcaagtg ctcgacgccc attatgactc   7860
agtcttaaag gacatcaagc tagcggcttc caaggtcagc gcaaggctcc tcaccttgga   7920
ggaggcgtgc cagttgactc cacccccattc tgcaagatcc aagtatggat tcggggccaa   7980
ggaggtccgc agcttgtccg ggagggccgt taaccacatc aagtccgtgt ggaaggacct   8040
cctggaagac ccacaaacac caattcccac aaccatcatg gccaaaaatg aggtgttctg   8100
cgtggacccc gccaagggg gtaagaaacc agctcgcctc atcgtttacc ctgacctcgg   8160
cgtccgggtc tgcgagaaaa tggccctcta tgacattaca caaaagcttc ctcaggcggt   8220
aatgggagct tcctatggct tccagtactc ccctgcccaa cgggtggagt atctcttgaa   8280
agcatgggcg gaaaagaagg accccatggg ttttcgtat gatacccgat gcttcgactc   8340
aaccgtcact gagagagaca tcaggaccga ggagtccata taccaggcct gctccctgcc   8400
cgaggaggcc cgcactgcca tacactcgct gactgagaga ctttacgtag gagggcccat   8460
gttcaacagc aagggtcaaa cctgcggtta cagacgttgc cgcgccagcg gggtgctaac   8520
cactagcatg ggtaacacca tcacatgcta tgtgaaagcc ctagcggcct gcaaggctgc   8580
ggggatagtt gcgcccacaa tgctggtatg cggcgatgac ctagtagtca tctcagaaag   8640
ccaggggact gaggaggacg agcggaacct gagagccttc acggaggcca tgaccaggta   8700
ctctgcccct cctggtgatc ccccagacc ggaatatgac ctggagctaa taacatcctg   8760
ttcctcaaat gtgtctgtgg cgttgggccc gcggggccgc cgcagatact acctgaccag   8820
agacccaacc actccactcg cccgggctgc ctgggaaaca gttagacact ccctatcaa    8880 ttcatgctg ggaaacatca tccagtatgc tccaaccata tgggttcgca tggtcctaat    8940
gacacacttc ttctccattc tcatggtcca agacaccctg gaccagaacc tcaactttga   9000
```

```
gatgtatgga tcagtatact ccgtgaatcc tttggacctt ccagccataa ttgagaggtt    9060
acacgggctt gacgccttt  ctatgcacac atactctcac cacgaactga cgcgggtggc    9120
ttcagccctc agaaaacttg gggcgccacc cctcagggtg tggaagagtc gggctcgcgc    9180
agtcagggcg tccctcatct cccgtggagg aaagcggcc  gtttgcggcc gatatctctt    9240
caattgggcg gtgaagacca agctcaaact cactccattg ccggaggcgc gcctactgga    9300
cttatccagt tggttcaccg tcggcgccgg cgggggcgac attttttcaca gcgtgtcgcg    9360 cgcccgaccc cgctcattac tcttcggcct actcctactt tcgtagggg  taggcctctt    9420 cctactcccc gctcggtaga gcggcacaca ctaggtacac tccatagcta actgttcctt    9480 ttttttttt  tttttttttt tttttttttt tttttttttt tcttttttt  tttttttcct    9540 cttcttccc  ttctcatctt attctacttt ctttcttggt ggctccatct tagccctagt    9600
cacggctagc tgtgaaaggt ccgtgagccg catgactgca gagagtgccg taactggtct    9660
ctctgcagat catgt                                                    9675

<210> SEQ ID NO 2
<211> LENGTH: 9666
<212> TYPE: DNA
<213> ORGANISM: Hepatitis C virus

<400> SEQUENCE: 2
acctgcccct aatagggcg  acactccgcc atgaatcact cccctgtgag gaactactgt     60
cttcacgcag aaagcgccta gccatggcgt tagtatgagt gtcgtacagc ctccaggccc    120
ccccctcccg ggagagccat agtggtctgc ggaaccggtg agtacaccgg aattgccggg    180
aagactgggt cctttcttgg ataaacccac tctatgcccg ccatttggg  cgtgcccccg    240 caagactgct agccgagtag cgttgggttg cgaaaggcct tgtggtactg cctgataggg    300
cgcttgcgag tgccccggga ggtctcgtag accgtgcacc atgagcacga atcctaaacc    360
tcaaagaaaa accaaacgta acaccaaccg tcgcccacag gacgtcaagt tcccgggtgg    420
cggtcagatc gttggtggag tttacttgtt gccgcgcagg ggccctagat gggtgtgcg    480 cgcgacgagg aagacttccg agcggtcgca acctcgaggt agacgtcagc ctatccccaa    540
ggcacgtcgg cccgagggca ggaccctggc tcagcccggg tacccttggc ccctctatgg    600
caatgagggt tgcgggtggg cgggatggct cctgtctccc cgtggctctc ggcctagctg    660 gggcccaca  gaccccggc  gtaggtcgcg caatttgggt aaggtcatcg ataccttac    720 gtgcggcttc gccgacctca tggggtacat accgctcgtc ggcgcccctc ttggaggcgc    780
tgccagggcc ctggcgcatg gcgtccgggt tctggaagac ggcgtgaact atgcaacagg    840
gaaccttcct ggttgctctt tctctatctt ccttctggcc ctgctctctt gcctgactgt    900
gcccgcttca gcctaccaag tgcgcaattc ctcgggctt  taccatgtca ccaatgattg    960
ccctaactcg agtattgtgt acgaggcggc cgatgccatc ctgcacactc ggggtgtgt    1020 cccttgcgtt cgcgagggta acgctcgag  gtgttgggtg gcggtgaccc ccacggtggc    1080
caccagggac ggcaaactcc ccacaacgca gcttcgacgt catatcgatc tgcttgtcgg    1140
gagcgccacc ctctgctcgg ccctctacgt gggggacctg tgcggtctg  tcttttcttgt    1200 tggtcaactg tttacccttct ctcccaggcg ccactggacg acgcaagact gcaattgttc    1260
tatctatccc ggccatataa cgggtcatcg catggcatgg gatatgatga tgaactggtc    1320
ccctacggca gcgttggtgg tagctcagct gctccggatc ccacaagcca tcatggacat    1380
```

-continued

```
gatcgctggt gctcactggg gagtcctggc gggcatagcg tatttctcca tggtggggaa    1440
ctgggcgaag gtcctggtag tgctgctgct atttgccggc gtcgacgcgg aaacccacgt    1500 caccgggga agtgccggcc gcaccacggc tgggcttgtt ggtctcctta caccaggcgc     1560
caagcagaac atccaactga tcaacaccaa cggcagttgg cacatcaata gcacggcctt    1620
gaactgcaat gaaagcctta acaccggctg gttagcaggg ctcttctatc agcacaaatt    1680
caactcttca ggctgtcctg agaggttggc cagctgccga cgccttaccg attttgccca    1740
gggctggggt cctatcagtt atgccaacgg aagcggcctc gacgaacgcc cctactgctg    1800
gcactaccct ccaagacctt gtggcattgt gcccgcaaag agcgtgtgtg gcccggtata    1860
ttgcttcact cccagccccg tggtggtggg aacgaccgac aggtcgggcg cgcctaccta    1920
cagctggggt gcaaatgata cggatgtctt cgtccttaac aacaccaggc caccgctggg    1980
caattggttc ggttgtacct ggatgaactc aactggattc accaaagtgt gcggagcgcc    2040
cccttgtgtc atcggagggg tgggcaacaa caccttgctc tgccccactg attgtttccg    2100
caagcatccg gaagccacat actctcggtg cggctccggt ccctggatta cacccaggtg    2160
catggtcgac tacccgtata ggctttggca ctatccttgt accatcaatt acaccatatt    2220
caaagtcagg atgtacgtgg gagggggtcga gcacaggctg gaagcggcct gcaactggac    2280
gcggggcgaa cgctgtgatc tggaagacag ggacaggtcc gagctcagcc cattgctgct    2340
gtccaccaca cagtggcagg tccttccgtg ttctttcacg accctgccag ccttgtccac    2400
cggcctcatc cacctccacc agaacattgt ggacgtgcag tacttgtacg ggtaggggtc    2460
aagcatcgcg tcctgggcca ttaagtggga gtacgtcgtt ctcctgttcc tcctgcttgc    2520
agacgcgcgc gtctgctcct gcttgtggat gatgttactc atatcccaag cggaggcggc    2580
tttggagaac ctcgtaatac tcaatgcagc atccctggcc gggacgcacg tcttgtgtc    2640 cttcctcgtg ttcttctgct ttgcgtggta tctgaagggt aggtgggtgc ccggagcggt    2700
ctacgccttc tacgggatgt ggcctctcct cctgctcctg ctggcgttgc ctcagcgggc    2760
atacgcactg gacacggagg tggccgcgtc gtgtggcggc gttgttcttg tcgggttaat    2820
ggcgctgact ctgtcgccat attacaagcg ctacatcagc tggtgcatgt ggtggcttca    2880
gtattttctg accagagtag aagcgcaact gcacgtgtgg gttccccccc tcaacgtccg    2940 ggggggcgc gatgccgtca tcttactcat gtgtgttgta cacccgactc tggtatttga    3000
catcaccaaa ctactcctgg ccatcttcgg accccctttgg attcttcaag ccagtttgct    3060
taaagtcccc tacttcgtgc gcgttcaagg ccttctccgg atctgcgcgc tagcgcggaa    3120
gatagccgga ggtcattacg tgcaaatggc catcatcaag ttagggggcgc ttactggcac    3180 ctatgtgtat aaccatctca cccctcttcg agactgggcg cacaacgcc tgcgagatct     3240 ggccgtggct gtggaaccag tcgtcttctc ccgaatggag accaagctca tcacgtgggg    3300
ggcagatacc gccgcgtgcg gtgacatcat caacggcttg cccgtctctg cccgtagggg    3360
ccaggagata ctgcttgggc cagccgacgg aatggtctcc aagggtgga ggttgctggc     3420 tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc cccctgggac caagtctttg gagccgtgca agtgtggagc    3720
cgtcgaccta tatctggtca cgcggaacgc tgatgtcatc ccggctcgga gacgcgggga    3780
```

-continued

```
caagcgggga gcattgctct ccccgagacc catttcgacc ttgaagggt cctcgggggg    3840 gccggtgctc tgccctaggg gccacgtcgt tgggctcttc cgagcagctg tgtgctctcg    3900
gggcgtggcc aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaacccctc ggtagctgcc accctggggt ttggggcgta    4140
cctatccaag gcacatggca tcaatcccaa cattaggact ggagtcagga ccgtgatgac    4200
cggggaggcc atcacgtact ccacatatgg caaatttctc gccgatgggg gctgcgctag    4260
cggcgcctat gacatcatca tatgcgatga atgccacgct gtggatgcta cctccattct    4320
cggcatcgga acggtccttg atcaagcaga gacagccggg gtcagactaa ctgtgctggc    4380
tacggccaca cccccgggt cagtgacaac ccccatccc gatatagaag ggtaggcct    4440 cgggcgggag ggtgagatcc ccttctatgg gagggcgatt cccctatcct gcatcaaggg    4500
agggagacac ctgattttct gccactcaaa gaaaaagtgt gacgagctcg cggcggccct    4560
tcggggcatg ggcttgaatg ccgtggcata ctatagaggg ttggacgtct ccataataccc    4620 agctcaggga gatgtggtgg tcgtcgccac cgacgccctc atgacggggt acactggaga    4680 cttttgactcc gtgatcgact gcaatgtagc ggtcacccaa gctgtcgact tcagcctgga    4740
ccccaccttc actataacca cacagactgt cccacaagac gctgtctcac gcagtcagcg    4800
ccgcgggcgc acaggtagag gaagacaggg cacttatagg tatgtttcca ctggtgaacg    4860
agcctcagga atgtttgaca gtgtagtgct ttgtgagtgc tacgacgcag gggctgcgtg    4920
gtacgatctc acaccagcgg agaccaccgt caggcttaga gcgtatttca acacgcccgg    4980
cctacccgtg tgtcaagacc atcttgaatt tggggagga gttttcaccg gcctcacaca    5040
catagacgcc cacttcctct cccaaacaaa gcaagcgggg gagaacttcg cgtacctagt    5100
agcctaccaa gctacggtgt gcgccagagc caaggcccct ccccgtcct gggacgccat    5160 gtggaagtgc ctgccccgac tcaagcctac gcttgcgggc cccacacctc tcctgtaccg    5220
tttgggccct attaccaatg aggtcaccct cacacaccct gggacgaagt acatcgccac    5280
atgcatgcaa gctgaccttg aggtcatgac cagcacgtgg gtcctagctg gaggagtcct    5340
ggcagccgtc gccgcatatt gcctggcgac tggatgcgtt tccatcatcg gccgcttgca    5400
cgtcaaccag cgagtcgtcg ttgcgccgga taaggaggtc ctgtatgagg cttttgatga    5460
gatggaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt tgggccagac acatgtggaa    5640
cttcattagc ggcatccaat acctcgcagg attgtcaaca ctgccaggga ccccgcggt    5700 ggcttccatg atggcattca gtgccgccct caccagtccg ttgtcgacca gtaccaccat    5760
ccttctcaac atcatgggag ctggttagc gtcccagatc gcaccacccg cgggggccac    5820
cggctttgtc gtcagtggcc tggtggggggc tgccgtgggc agcataggcc tgggtaaggt    5880
gctggtggac atcctggcag gatatggtgc gggcatttcg ggggccctcg tcgcattcaa    5940
gatcatgtct ggcgagaagc cctctatgga agatgtcatc aatctactgc ctgggatcct    6000
gtctccggga gccctggtgg tgggggtcat ctgcgcggcc attctgcgcc gccacgtggg    6060
accgggggag ggcgcggtcc aatggatgaa caggcttatt gcctttgctt ccagaggaaa    6120
```

```
ccacgtcgcc cctactcact acgtgacgga gtcggatgcg tcgcagcgtg tgacccaact      6180
acttggctct cttactataa ccagcctact cagaagactc cacaattgga taactgagga      6240
ctgccccatc ccatgctccg gatcctggct ccgcgacgtg tgggactggg tttgcaccat      6300
cttgacagac ttcaaaaatt ggctgacctc taaattgttc cccaagctgc ccggcctccc      6360
cttcatctct tgtcaaaagg ggtacaaggg tgtgtgggcc ggcactggca tcatgaccac      6420
gcgctgccct tgcggcgcca acatctctgg caatgtccgc ctgggctcta tgaggatcac      6480
agggcctaaa acctgcatga acacctggca ggggaccttt cctatcaatt gctacacgga      6540
gggccagtgc gcgccgaaac cccccacgaa ctacaagacc gccatctgga gggtggcggc      6600
ctcggagtac gcggaggtga cgcagcatgg gtcgtactcc tatgtaacag gactgaccac      6660
tgacaatctg aaaattcctt gccaactacc ttctccagag ttttttctcct gggtggacgg      6720 tgtgcagatc cataggtttg cacccacacc aaagccgttt ttccgggatg aggtctcgtt      6780
ctgcgttggg cttaattcct atgctgtcgg gtcccagctt ccctgtgaac ctgagcccga      6840
cgcagacgta ttgaggtcca tgctaacaga tccgccccac atcacggcgg agactgcggc      6900
gcggcgcttg gcacggggat cacctccatc tgaggcgagc tcctcagtga gccagctatc      6960
agcaccgtcg ctgcgggcca cctgcaccac ccacagcaac acctatgacg tggacatggt      7020
cgatgccaac ctgctcatgg agggcggtgt ggctcagaca gagcctgagt ccagggtgcc      7080
cgttctggac tttctcgagc caatggccga ggaagagagc gaccttgagc cctcaatacc      7140
atcggagtgc atgctcccca ggagcgggtt tccacgggcc ttaccggctt gggcacggcc      7200
tgactacaac ccgccgctcg tggaatcgtg gaggaggcca gattaccaac cgcccaccgt      7260
tgctggttgt gctctccccc cccccaagaa ggccccgacg cctcccccaa ggagacgccg      7320
gacagtgggt ctgagcgaga gcaccatatc agaagccctc cagcaactgg ccatcaagac      7380 cttttggccag ccccctcga gcggtgatgc aggctcgtcc acgggggcgg gcgccgccga      7440
atccggcggt ccgacgtccc ctggtgagcc ggcccctca gagacaggtt ccgcctcctc      7500 tatgccccc ctcgagggggg agcctggaga tccggacctg gagtctgatc aggtagagct      7560
tcaacctccc ccccaggggg gggggtagc tcccggttcg ggctcggggt cttggtctac      7620
ttgctccgag gaggacgata ccaccgtgtg ctgctccatg tcatactcct ggaccggggc      7680
tctaataact ccctgtagcc ccgaagagga aaagttgcca atcaacccctt tgagtaactc      7740 gctgttgcga taccataaca aggtgtactg tacaacatca aagagcgcct cacagagggc      7800 taaaaggta acttttgaca ggacgcaagt gctcgacgcc cattatgact cagtcttaaa      7860
ggacatcaag ctagcggctt ccaaggtcag cgcaaggctc ctcaccttgg aggaggcgtg      7920
ccagttgact ccacccccatt ctgcaagatc caagtatgga ttcggggcca aggaggtccg      7980
cagcttgtcc gggagggccg ttaaccacat caagtccgtg tggaaggacc tcctggaaga      8040
cccacaaaca ccaattccca caaccatcat ggccaaaaat gaggtgttct gcgtggaccc      8100
cgccaagggg ggtaagaaac cagctcgcct catcgtttac cctgacctcg gcgtccgggt      8160
ctgcgagaaa atggccctct atgacattac acaaaagctt cctcaggcgg taatgggagc      8220
ttcctatggc ttccagtact cccctgccca acgggtggag tatctcttga agcatgggc      8280 ggaaaagaag gaccccatgg gttttttcgta tgatacccga tgcttcgact caaccgtcac      8340
tgagagagac atcaggaccg aggagtccat ataccaggcc tgctccctgc ccgaggaggc      8400
ccgcactgcc atacactcgc tgactgagag actttacgta ggagggccca tgttcaacag      8460
caagggtcaa acctgcggtt acagacgttg ccgcgccagc ggggtgctaa ccactagcat      8520
```

-continued

```
gggtaacacc atcacatgct atgtgaaagc cctagcggcc tgcaaggctg cggggatagt      8580
tgcgcccaca atgctggtat gcggcgatga cctagtagtc atctcagaaa gccaggggac      8640
tgaggaggac gagcggaacc tgagagcctt cacggaggcc atgaccaggt actctgcccc      8700
tcctggtgat cccccagac cggaatatga cctggagcta ataacatcct gttcctcaaa       8760
tgtgtctgtg gcgttgggcc cgcggggccg ccgcagatac tacctgacca gagacccaac      8820
cactccactc gcccgggctg cctgggaaac agttagacac tccctatca attcatggct       8880
gggaaacatc atccagtatg ctccaaccat atgggttcgc atggtcctaa tgacacactt      8940
cttctccatt ctcatggtcc aagacaccct ggaccagaac ctcaactttg agatgtatgg      9000
atcagtatac tccgtgaatc ctttggacct tccagccata attgagaggt tacacgggct      9060
tgacgccttt tctatgcaca catactctca ccacgaactg acgcgggtgg cttcagccct      9120
cagaaaactt ggggcgccac ccctcagggt gtggaagagt cgggctcgcg cagtcagggc      9180
gtccctcatc tcccgtggag ggaaagcggc cgtttgcggc cgatatctct tcaattgggc      9240
ggtgaagacc aagctcaaac tcactccatt gccggaggcg cgcctactgg acttatccag      9300
ttggttcacc gtcggcgccg gcgggggcga catttttcac agcgtgtcgc gcgcccgacc      9360
ccgctcatta ctcttcggcc tactcctact tttcgtaggg gtaggcctct tcctactccc      9420
cgctcggtag agcggcacac actaggtaca ctccatagct aactgttcct ttttttttt       9480
tttttttttt tttttttttt tttttttttt ttctttttttt tttttttccc tctttcttcc     9540
cttctcatct tattctactt tctttcttgg tggctccatc ttagccctag tcacggctag      9600
ctgtgaaagg tccgtgagcc gcatgactgc agagagtgcc gtaactggtc tctctgcaga      9660
tcatgt                                                                 9666
```

<210> SEQ ID NO 3
<211> LENGTH: 9666
<212> TYPE: DNA
<213> ORGANISM: Hepatitis C virus

<400> SEQUENCE: 3

```
acctgcccct aatagggcg acactccgcc atgaatcact cccctgtgag gaactactgt       60
cttcacgcag aaagcgccta gccatggcgt tagtatgagt gtcgtacagc ctccaggccc      120
cccctcccg ggagagccat agtggtctgc ggaaccggtg agtacaccgg aattgccggg       180
aagactgggt cctttcttgg ataaacccac tctatgcccg gccatttggg cgtgcccccg      240
caagactgct agccgagtag cgttgggttg cgaaaggcct tgtggtactg cctgataggg      300
cgcttgcgag tgccccggga ggtctcgtag accgtgcacc atgagcacga atcctaaacc      360
tcaaagaaaa accaaccgta acaccaaccg tcgcccacag gacgtcaagt tcccgggtgg      420
cggtcagatc gttggtggag tttacttgtt gccgcgcagg ggccctagat tgggtgtgcg      480
cgcgacgagg aagacttccg agcggtcgca acctcgaggt agacgtcagc ctatccccaa      540
ggcacgtcgg cccgagggca ggacctgggc tcagcccggg tacccttggc ccctctatgg      600
caatgagggt tgcgggtggg cgggatggct cctgtctccc cgtggctctc ggcctagctg      660
gggcccccaca ccccggcgtg gtcgcgcg caatttgggt aaggtcatcg ataccttac        720
gtgcggcttc gccgacctca tggggtacat accgctcgtc ggcgcccctc ttggaggcgc      780
tgccagggcc ctggcgcatg gcgtccgggt tctggaagac ggcgtgaact atgcaacagg      840
gaaccttcct ggttgctctt tctctatctt ccttctggcc ctgctctctt gcctgactgt      900
```

```
gcccgcttca gcctaccaag tgcgcaattc ctcggggctt taccatgtca ccaatgattg      960
ccctaactcg agtattgtgt acgaggcggc cgatgccatc ctgcacactc cggggtgtgt     1020
cccttgcgtt cgcgagggta acgcctcgag gtgttgggtg gcggtgaccc ccacggtggc     1080
caccagggac ggcaaactcc ccacaacgca gcttcgacgt catatcgatc tgcttgtcgg     1140
gagcgccacc ctctgctcgg ccctctacgt gggggacctg tgcgggtctg tctttcttgt     1200
tggtcaactg tttaccttct ctcccaggcg ccactggacg acgcaagact gcaattgttc     1260
tatctatccc ggccatataa cgggtcatcg catggcatgg gatatgatga tgaactggtc     1320
ccctacggca gcgttggtgg tagctcagct gctccggatc ccacaagcca tcatggacat     1380
gatcgctggt gctcactggg gagtcctggc gggcatagcg tatttctcca tggtggggaa     1440
ctgggcgaag gtcctggtag tgctgctgct atttgccggc gtcgacgcgg aaacccacgt     1500
caccggggga agtgccggcc gcaccacggc tgggcttgtt ggtctcctta caccaggcgc     1560
caagcagaac atccaactga tcaacaccaa cggcagttgg cacatcaata gcacggcctt     1620
gaactgcaat gaaagcctta acaccggctg gttagcaggg ctcttctatc agcacaaatt     1680
caactcttca ggctgtcctg agaggttggc cagctgccga cgccttaccg attttgccca     1740
gggctggggt cctatcagtt atgccaacgg aagcggcctc gacgaacgcc cctactgctg     1800
gcactaccct ccaagacctt gtggcattgt cccgcaaag agcgtgtgtg gcccggtata     1860
ttgcttcact cccagccccg tggtggtggg aacgaccgac aggtcgggcg cgcctaccta     1920
cagctggggt gcaaatgata cggatgtctt cgtccttaac aacaccaggc caccgctggg     1980
caattggttc ggttgtacct ggatgaactc aactggattc accaaagtgt gcggagcgcc     2040
cccttgtgtc atcggagggg tgggcaacaa caccttgctc tgccccactg attgtttccg     2100
caagcatccg gaagccacat actctcggtg cggctccggt ccctggatta cacccaggtg     2160
catggtcgac tacccgtata ggcttttggca ctatccttgt accatcaatt acaccatatt     2220
caaagtcagg atgtacgtgg gaggggtcga gcacaggctg gaagcggcct gcaactggac     2280
gcggggcgaa cgctgtgatc tggaagacag ggacaggtcc gagctcagcc cattgctgct     2340
gtccaccaca cagtggcagg tccttccgtg ttctttcacg accctgccag ccttgtccac     2400
cggcctcatc cacctccacc agaacattgt ggacgtgcag tacttgtacg gggtagggtc     2460
aagcatcgcg tcctgggcca ttaagtggga gtacgtcgtt ctcctgttcc tcctgcttgc     2520
agacgcgcgc gtctgctcct gcttgtggat gatgttactc atatcccaag cggaggcggc     2580
tttggagaac ctcgtaatac tcaatgcagc atccctggcc gggacgcacg tcttgtgtc      2640
cttcctcgtg ttcttctgct ttgcgtggta tctgaagggt aggtgggtgc ccggagcggt     2700
ctacgccttc tacgggatgt ggcctctcct cctgctcctg ctggcgttgc ctcagcgggc     2760
atacgcactg gacacggagg tggccgcgtc gtgtggcggc gttgttcttg tcgggttaat     2820
ggcgctgact ctgtcgccat attacaagcg ctacatcagc tggtgcatgt ggtggcttca     2880
gtatttctgg accagagtag aagcgcaact gcacgtgtgg gttccccccc tcaacgtccg     2940
ggggggggcgc gatgccgtca tcttactcat gtgtgttgta cacccgactc tggtatttga     3000
catcaccaaa ctactcctgg ccatcttcgg acccctttgg attcttcaag ccagtttgct     3060
taaagtcccc tacttcgtgc gcgttcaagg ccttctccgg atctgcgcgc tagcgcggaa     3120
gatagccgga ggtcattacg tgcaaatggc catcatcaag ttaggggcgc ttactggcac     3180
ctatgtgtat aaccatctca cccctcttcg agactgggcg cacaacgcc tgcgagatct      3240
ggccgtggct gtggaaccag tcgtcttctc ccgaatggag accaagctca tcacgtgggg     3300
```

```
ggcagatacc gccgcgtgcg gtgacatcat caacggcttg cccgtctctg cccgtagggg   3360
ccaggagata ctgcttgggc cagccgacgg aatggtctcc aaggggtgga ggttgctggc   3420
tcccatcact gcttatgccc agcaaacacg aggcctcctg ggcgccatag tggtgagtat   3480
gacggggcgt gacaggacag aacaggccgg ggaagtccaa atcctgtcca cagtctctca   3540
gtccttcctc ggaacaacca tctcgggggt tttgtggact gtttaccacg gagctggcaa   3600
caagactcta gccggcttac ggggtccggt cacgcagatg tactcgagtg ctgagggga    3660 cttggtaggc tggcccagcc ccctgggac caagtctttg gagccgtgca agtgtggagc    3720
cgtcgaccta tatctggtca cgcggaacgc tgatgtcatc ccggctcgga gacgcgggga   3780
caagcgggga gcattgctct ccccgagacc catttcgacc ttgaaggggt cctcgggggg   3840
gccggtgctc tgccctaggg gccacgtcgt tgggctcttc cgagcagctg tgtgctctcg   3900
gggcgtggcc aaatccatcg atttcatccc cgttgagaca ctcgacgttg ttacaaggtc   3960
tcccactttc agtgacaaca gcacgccacc ggctgtgccc cagacctatc aggtcgggta   4020
cttgcatgct ccaactggca gtggaaagag caccaaggtc cctgtcgcgt atgccgccca   4080
ggggtacaaa gtactagtgc ttaacccctc ggtagctgcc accctgggt ttggggcgta    4140 cctatccaag gcatggca tcaatcccaa cattaggact ggagtcagga ccgtgatgac     4200
cggggaggcc atcacgtact ccacatatgg caaatttctc gccgatgggg gctgcgctag   4260
cggcgcctat gacatcatca tatgcgatga atgccacgct gtggatgcta cctccattct   4320
cggcatcgga acggtccttg atcaagcaga dacagccggg gtcagactaa ctgtgctggc   4380
tacggccaca ccccccgggt cagtgacaac ccccatccc gatatagaag aggtaggcct    4440
cgggcgggag ggtgagatcc ccttctatgg gagggcgatt cccctatcct gcatcaaggg   4500
agggagacac ctgatttct gccactcaaa gaaaaagtgt gacgagctcg cggcggccct    4560
tcggggcatg ggcttgaatg ccgtggcata ctatagaggg ttggacgtct ccataatacc   4620
agctcaggga gatgtggtgg tcgtcgccac cgacgccctc atgacggggt acactggaga   4680 cttttgactcc gtgatcgact gcaatgtagc ggtcacccaa gctgtcgact tcagcctgga  4740
ccccaccttc actataacca cacagactgt cccacaagac gctgtctcac gcagtcagcg   4800
ccgcgggcgc acaggtagag gaagacaggg cacttatagg tatgtttcca ctggtgaacg   4860
agcctcagga atgtttgaca gtgtagtgct tgtgagtgc tacgacgcag ggctgcgtg     4920 gtacgatctc acaccagcgg agaccaccgt caggcttaga gcgtatttca acacgcccgg   4980
cctacccgtg tgtcaagacc atcttgaatt tggggaggca gttttcaccg gcctcacaca   5040
catagacgcc cacttcctct cccaaacaaa gcaagcgggg gagaacttcg cgtacctagt   5100
agcctaccaa gctacggtgt gcgccagagc caaggcccct ccccgtcct gggacgccat    5160 gtggaagtgc ctggcccgac tcaagcctac gcttgcgggc cccacacctc tcctgtaccg   5220
tttgggccct attaccaatg aggtcacccc cacacaccct gggacgaagt acatcgccac   5280
atgcatgcaa gctgaccttg aggtcatgac cagcacgtgg gtcctagctg gaggagtcct   5340
ggcagccgtc gccgcatatt gcctggcgac tggatgcgtt tccatcatcg gccgcttgca   5400
cgtcaaccag cgagtcgtcg ttgcgccgga taaggaggtc ctgtatgagg cttttgatga   5460
gatggaggaa tgcgcctcta gggcggctct catcgaagag gggcagcgga tagccgagat   5520
gttgaagtcc aagatccaag gcttgctgca gcaggcctct aagcaggccc aggacataca   5580
acccgctatg caggcttcat ggcccaaagt ggaacaattt tgggcagac acatgtggaa    5640
```

```
cttcattagc ggcatccaat acctcgcagg attgtcaaca ctgccaggga accccgcggt    5700
ggcttccatg atggcattca gtgccgccct caccagtccg ttgtcgacca gtaccaccat    5760
ccttctcaac atcatgggag ctggttagc gtcccagatc gcaccacccg cgggggccac     5820
cggctttgtc gtcagtggcc tggtggggc tgccgtgggc agcataggcc tgggtaaggt     5880
gctggtggac atcctggcag gatatggtgc gggcatttcg ggggccctcg tcgcattcaa    5940
gatcatgtct ggcgagaagc cctctatgga agatgtcatc aatctactgc ctgggatcct    6000
gtctccggga gccctggtgg tgggggtcat ctgcgcggcc attctgcgcc gccacgtggg    6060
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggacctttt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttttctcct gggtggacgg    6720 tgtgcagatc cataggttttg cacccacacc aaagccgtttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctcccccaa ggagacgccg    7320
gacagtgggt ctgagcgaga gcaccatatc agaagccctc cagcaactgg ccatcaagac    7380
ctttggccag ccccctcga gcggtgatgc aggctcgtcc acggggcgg gcgccgccga    7440 atccggcggt ccgacgtccc ctggtgagcc ggcccccctca gagacaggtt ccgcctcctc    7500 tatgccccc ctcgagggg agcctggaga tccggacctg gagtctgatc aggtagagct    7560
tcaacctccc ccccaggggg gggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaacccctt tgagtaactc    7740 gctgttgcga taccataaca aggtgtactg tacaacatca aagagcgcct cacagagggc    7800
taaaaaggta acttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccaccccatt ctgcaagatc caagtatgga ttcggggcca aggaggtccg    7980
cagcttgtcc gggagggccg ttaaccacat caagtccgtg tggaaggacc tcctggaaga    8040
```

-continued

```
cccacaaaca ccaattccca caaccatcat ggccaaaaat gaggtgttct gcgtggaccc    8100
cgccaagggg ggtaagaaac cagctcgcct catcgtttac cctgacctcg cgtccgggt    8160
ctgcgagaaa atggccctct atgacattac acaaaagctt cctcaggcgg taatgggagc    8220
ttcctatggc ttccagtact cccctgccca acgggtggag tatctcttga agcatgggc    8280
ggaaaagaag acccccatgg ttttttcgta tgatacccga tgcttcgact caaccgtcac    8340
tgagagagac atcaggaccg aggagtccat ataccaggcc tgctccctgc ccgaggaggc    8400
ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccaggggac    8640
tgaggaggac gagcggaacc tgagagcctt cacggaggcc atgaccaggt actctgcccc    8700
tcctggtgat cccccagac cggaatatga cctggagcta ataacatcct gttcctcaaa    8760
tgtgtctgtg gcgttgggcc cgcggggccg ccgcagatac tacctgacca gagacccaac    8820
cactccactc gcccgggctg cctgggaaac agttagacac tccctatca attcatggct    8880
gggaaacatc atccagtatg ctccaaccat atgggttcgc atggtcctaa tgacacactt    8940
cttctccatt ctcatggtcc aagacacctt ggaccagaac ctcaactttg agatgtatgg    9000
atcagtatac tccgtgaatc ctttggacct tccagccata attgagaggt acacgggct    9060
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcgggggcga cattttcac agcgtgtcgc gcgcccgacc    9360
ccgctcatta ctcttcggcc tactcctact tttcgtaggg gtaggcctct cctactccc    9420
cgctcggtag agcggcacac actaggtaca ctccatagct aactgttcct ttttttttt    9480
ttttttttt tttttttt ttttttttt ttctttttt tttttttccc tcttcttcc    9540
cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                              9666
```

<210> SEQ ID NO 4
<211> LENGTH: 9666
<212> TYPE: DNA
<213> ORGANISM: Hepatitis C virus

<400> SEQUENCE: 4

```
acctgcccct aatagggcg acactccgcc atgaatcact cccctgtgag gaactactgt      60
cttcacgcag aaagcgccta gccatggcgt tagtatgagt gtcgtacagc ctccaggccc     120
cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttggggttg cgaaaggcct tgtggtactg cctgataggg     300
cgcttgcgag tgccccggga ggtctcgtag accgtgcacc atgagcacga atcctaaacc     360
tcaaagaaaa accaaacgta acaccaaccg tcgcccacag gacgtcaagt tcccgggtgg     420
```

-continued

```
cggtcagatc gttggtggag tttacttgtt gccgcgcagg ggccctagat tgggtgtgcg    480
cgcgacgagg aagacttccg agcggtcgca acctcgaggt agacgtcagc ctatccccaa    540
ggcacgtcgg cccgagggca ggacctgggc tcagcccggg taccctggcc cctctatgg     600
caatgagggt tgcgggtggg cgggatggct cctgtctccc cgtggctctc ggcctagctg    660
gggccccaca gaccccggc gtaggtcgcg caatttgggt aaggtcatcg ataccttac      720
gtgcggcttc gccgacctca tggggtacat accgctcgtc ggcgccctc ttggaggcgc     780
tgccagggcc ctggcgcatg gcgtccgggt tctggaagac ggcgtgaact atgcaacagg    840
gaaccttcct ggttgctctt tctctatctt ccttctggcc ctgctctctt gcctgactgt    900
gcccgcttca gcctaccaag tgcgcaattc ctcgggctt taccatgtca ccaatgattg     960
ccctaactcg agtattgtgt acgaggcggc cgatgccatc ctgcacactc ggggtgtgt    1020
cccttgcgtt cgcgagggta acgcctcgag gtgttgggtg gcggtgaccc ccacggtggc   1080
caccagggac ggcaaactcc ccacaacgca gcttcgacgt catatcgatc tgcttgtcgg   1140
gagcgccacc ctctgctcgg ccctctacgt gggggacctg tgcgggtctg tctttcttgt   1200
tggtcaactg tttaccttct ctcccaggcg ccactggacg acgcaagact gcaattgttc   1260
tatctatccc ggccatataa cgggtcatcg catggcatgg gatatgatga tgaactggtc   1320
ccctacggca gcgttggtgg tagctcagct gctccggatc ccacaagcca tcatggacat   1380
gagcgctggt gctcactggg gagtcctggc gggcatagcg tatttctcca tggtggggaa   1440
ctgggcgaag gtcctggtag tgctgctgct atttgccggc gtcgacgcgg aaacccacgt   1500
caccggggga agtgccggcc gcaccacggc tgggcttgtt ggtctcctta caccaggcgc   1560
caagcagaac atccaactga tcaacaccaa cggcagttgg cacatcaata gcacggcctt   1620
gaactgcaat gaaagcctta acaccggctg gttagcaggg ctcttctatc agcacaaatt   1680
caactcttca ggctgtcctg agaggttggc cagctgccga cgccttaccg attttgccca   1740
gggctgggt cctatcagtt atgccaacgg aagcggcctc gacgaacgcc cctactgctg    1800
gcactaccct ccaagacctt gtggcattgt gcccgcaaag agcgtgtgtg gcccggtata   1860
ttgcttcact cccagccccg tggtggtggg aacgaccgac aggtcgggcg cgcctaccta   1920
cagctggggt gcaaatgata cggatgtctt cgtccttaac aacaccaggc caccgctggg   1980
caattggttc ggttgtacct ggatgaactc aactggattc accaaagtgt gcggagcgcc   2040
cccttgtgtc atcggagggg tgggcaacaa caccttgctc tgccccactg attgtttccg   2100
caagcatccg gaagccacat actctcggtg cggctccggt ccctggatta cacccaggtg   2160
catggtcgac tacccgtata ggctttggca ctatccttgt accatcaatt acaccatatt   2220
caaagtcagg atgtacgtgg gagggtcga gcacaggctg gaagcggcct gcaactggac   2280
gcggggcgaa cgctgtgatc tggaagacag ggacaggtcc gagctcagcc cattgctgct   2340
gtccaccaca cagtggcagg tccttccgtg ttctttcacg accctgccag ccttgtccac   2400
cggcctcatc cacctccacc agaacattgt ggacgtgcag tacttgtacg gggtagggtc   2460
aagcatcgcg tcctgggcca ttaagtggga gtacgtcgtt ctcctgttcc tcctgcttgc   2520
agacgcgcgc gtctgctcct gcttgtggat gatgttactc atatcccaag cggaggcggc   2580
tttggagaac ctcgtaatac tcaatgcagc atccctggcc gggacgcacg gtcttgtgtc   2640
cttcctcgtg ttcttctgct ttgcgtggta tctgaagggt aggtgggtgc ccggagcggt   2700
ctacgccttc tacgggatgt ggcctctcct cctgctcctg ctggcgttgc ctcagcgggc   2760
atacgcactg gacacggagg tggccgcgtc gtgtggcggc gttgttcttg tcgggttaat   2820
```

```
ggcgctgact ctgtcgccat attacaagcg ctacatcagc tggtgcatgt ggtggcttca    2880
gtattttctg accagagtag aagcgcaact gcacgtgtgg gttccccccc tcaacgtccg    2940 ggggggggcgc gatgccgtca tcttactcat gtgtgttgta cacccgactc tggtatttga    3000
catcaccaaa ctactcctgg ccatcttcgg accccttttgg attcttcaag ccagtttgct    3060
taaagtcccc tacttcgtgc gcgttcaagg ccttctccgg atctgcgcgc tagcgcggaa    3120
gatagccgga ggtcattacg tgcaaatggc catcatcaag ttaggggcgc ttactggcac    3180
ctatgtgtat aaccatctca cccctcttcg agactgggcg cacaacggcc tgcgagatct    3240
ggccgtggct gtggaaccag tcgtcttctc ccgaatggag accaagctca tcacgtgggg    3300
ggcagatacc gccgcgtgcg gtgacatcat caacggcttg cccgtctctg cccgtagggg    3360
ccaggagata ctgcttgggc cagccgacgg aatggtctcc aaggggtgga ggttgctggc    3420
tcccatcact gctatgcccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc ccctgggac caagtctttg gagccgtgca agtgtggagc    3720
cgtcgaccta tatctggtca cgcggaacgc tgatgtcatc ccggctcgga gacgcgggga    3780
caagcgggga gcattgctct ccccgagacc catttcgacc ttgaaggggt cctcgggggg    3840
gccggtgctc tgccctaggg gccacgtcgt tgggctcttc cgagcagctg tgtgctctcg    3900
gggcgtggcc aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaaccccct ggtagctgcc accctggggt ttgggcgta    4140 cctatccaag gcacatggca tcaatcccaa cattaggact ggagtcagga ccgtgatgac    4200
cggggaggcc atcacgtact ccacatatgg caaatttctc gccgatgggg gctgcgctag    4260
cggcgcctat gacatcatca tatgcgatga atgccacgct gtggatgcta cctccattct    4320
cggcatcgga acggtccttg atcaagcaga gacagccggg gtcagactaa ctgtgctggc    4380
tacggccaca ccccccgggt cagtgacaac ccccccatccc gatatagaag aggtaggcct    4440
cgggcgggag ggtgagatcc ccttctatgg gagggcgatt cccctatcct gcatcaaggg    4500
agggagacac ctgattttct gccactcaaa gaaaaagtgt gacgagctcg cggcggccct    4560
tcggggcatg ggcttgaatg ccgtggcata ctatagaggg ttggacgtct ccataatacc    4620
agctcaggga gatgtggtgg tcgtcgccac cgacgccctc atgacggggt acactggaga    4680
ctttgactcc gtgatcgact gcaatgtagc ggtcacccaa gctgtcgact tcagcctgga    4740
ccccaccttc actataacca cacagactgt cccacaagac gctgtctcac gcagtcagcg    4800
ccgcgggcgc acaggtagag gaagacaggg cacttatagg tatgtttcca ctggtgaacg    4860
agcctcagga atgtttgaca gtgtagtgct ttgtgagtgc tacgacgcag ggctgcgtg    4920 gtacgatctc acaccagcgg agaccaccgt caggcttaga gcgtatttca acacgcccgg    4980
cctacccgtg tgtcaagacc atcttgaatt ttggaggca gttttcaccg gcctcacaca    5040
catagacgcc cacttcctct cccaaacaaa gcaagcgggg gagaacttcg cgtacctagt    5100
agcctaccaa gctacggtgt gcgccagagc caaggcccct ccccgtcct gggacgccat    5160
```

-continued

```
gtggaagtgc ctggcccgac tcaagcctac gcttgcgggc cccacacctc tcctgtaccg   5220 tttgggcccct attaccaatg aggtcaccct cacacacctc gggacgaagt acatcgccac   5280
atgcatgcaa gctgaccttg aggtcatgac cagcacgtgg gtcctagctg gaggagtcct   5340
ggcagccgtc gccgcatatt gcctggcgac tggatgcgtt ccatcatcg gccgcttgca   5400 cgtcaaccag cgagtcgtcg ttgcgccgga taaggaggtc ctgtatgagg cttttgatga   5460
gatggaggaa tgcgcctcta gggcggctct catcgaagag gggcagcgga tagccgagat   5520
gttgaagtcc aagatccaag gcttgctgca gcaggcctct aagcaggccc aggacataca   5580
acccgctatg caggcttcat ggcccaaagt ggaacaattt tgggccagac acatgtggaa   5640
cttcattagc ggcatccaat acctcgcagg attgtcaaca ctgccaggga accccgcggt   5700
ggcttccatg atggcattca gtgccgccct caccagtccg ttgtcgacca gtaccaccat   5760
ccttctcaac atcatgggag gctggttagc gtcccagatc gcaccacccg cggggggccac   5820 cggctttgtc gtcagtggcc tggtggggc tgccgtgggc agcataggcc tgggtaaggt   5880
gctggtggac atcctggcag gatatggtgc gggcatttcg ggggccctcg tcgcattcaa   5940
gatcatgtct ggcgagaagc cctctatgga agatgtcatc aatctactgc ctgggatcct   6000
gtctccggga gccctggtgg tgggggtcat ctgcgcggcc attctgcgcc gccacgtggg   6060 accggggag ggcgcggtcc aatggatgaa caggcttatt gcctttgctt ccagaggaaa   6120
ccacgtcgcc cctactcact acgtgacgga gtcggatgcg tcgcagcgtg tgacccaact   6180
acttggctct cttactataa ccagcctact cagaagactc cacaattgga taactgagga   6240
ctgccccatc ccatgctccg gatcctggct ccgcgacgtg tgggactggg tttgcaccat   6300
cttgacagac ttcaaaaatt ggctgacctc taaattgttc cccaagctgc ccggcctccc   6360
cttcatctct tgtcaaaagg ggtacaaggg tgtgtgggcc ggcactggca tcatgaccac   6420
gcgctgccct tgcggcgcca acatctctgg caatgtccgc ctgggctcta tgaggatcac   6480
agggcctaaa acctgcatga acacctggca ggggacctttt cctatcaatt gctacacgga   6540
gggccagtgc gcgccgaaac cccccacgaa ctacaagacc gccatctgga gggtggcggc   6600
ctcggagtac gcggaggtga cgcagcatgg gtcgtactcc tatgtaacag gactgaccac   6660
tgacaatctg aaaattcctt gccaactacc ttctccagag ttttttctcct gggtggacgg   6720 tgtgcagatc cataggtttg cacccacacc aaagccgttt ttccgggatg aggtctcgtt   6780
ctgcgttggg cttaattcct atgctgtcgg gtcccagctt ccctgtgaac ctgagcccga   6840
cgcagacgta ttgaggtcca tgctaacaga tccgccccac atcacggcgg agactgcggc   6900
gcggcgcttg gcacggggat cacctccatc tgaggcgagc tcctcagtga gccagctatc   6960
agcaccgtcg ctgcgggcca cctgcaccac ccacagcaac acctatgacg tggacatggt   7020
cgatgccaac ctgctcatgg agggcggtgt ggctcagaca gagcctgagt ccaggtgcc   7080 cgttctggac tttctcgagc caatggccga ggaagagagc gaccttgagc cctcaatacc   7140
atcggagtgc atgctcccca ggagcgggtt tccacgggcc ttaccggctt gggcacggcc   7200
tgactacaac ccgccgctcg tggaatcgtg gaggaggcca gattaccaac cgcccaccgt   7260
tgctggttgt gctctccccc ccccaagaa ggccccgacg cctcccccaa ggagacgccg   7320
gacagtgggt ctgagcgaga gcaccatatc agaagccctc cagcaactgg ccatcaagac   7380
ctttggccag ccccctcga gcggtgatgc aggctcgtcc acggggggcgg gcgccgccga   7440 atccggcggt ccgacgtccc ctggtgagcc ggccccctca gagacaggtt ccgcctcctc   7500 tatgccccccc ctcgagggg agcctggaga tccggacctg gagtctgatc aggtagagct   7560
```

-continued

```
tcaacctccc ccccaggggg ggggggtagc tcccggttcg ggctcggggt cttggtctac   7620
ttgctccgag gaggacgata ccaccgtgtg ctgctccatg tcatactcct ggaccggggc   7680
tctaataact ccctgtagcc ccgaagagga aaagttgcca atcaaccctt tgagtaactc   7740
gctgttgcga taccataaca aggtgtactg tacaacatca aagagcgcct cacagagggc   7800
taaaaaggta acttttgaca ggacgcaagt gctcgacgcc cattatgact cagtcttaaa   7860
ggacatcaag ctagcggctt ccaaggtcag cgcaaggctc ctcaccttgg aggaggcgtg   7920
ccagttgact ccaccccatt ctgcaagatc caagtatgga ttcggggcca aggaggtccg   7980
cagcttgtcc gggagggccg ttaaccacat caagtccgtg tggaaggacc tcctggaaga   8040
cccacaaaca ccaattccca caaccatcat ggccaaaaat gaggtgttct gcgtggaccc   8100
cgccaagggg ggtaagaaac cagctcgcct catcgtttac cctgacctcg gcgtccgggt   8160
ctgcgagaaa atggccctct atgacattac acaaaagctt cctcaggcgg taatgggagc   8220
ttcctatggc ttccagtact cccctgccca acgggtggag tatctcttga aagcatgggc   8280
ggaaaagaag gaccccatgg gtttttcgta tgatacccga tgcttcgact caaccgtcac   8340
tgagagagac atcaggaccg aggagtccat ataccaggcc tgctccctgc ccgaggaggc   8400
ccgcactgcc atacactcgc tgactgagag actttacgta ggagggccca tgttcaacag   8460
caagggtcaa acctgcggtt acagacgttg ccgcgccagc ggggtgctaa ccactagcat   8520
gggtaacacc atcacatgct atgtgaaagc cctagcggcc tgcaaggctg cggggatagt   8580
tgcgcccaca atgctggtat gcggcgatga cctagtagtc atctcagaaa gccaggggac   8640
tgaggaggac gagcggaacc tgagagcctt cacggaggcc atgaccaggt actctgcccc   8700
tcctggtgat ccccccagac cggaatatga cctggagcta ataacatcct gttcctcaaa   8760
tgtgtctgtg gcgttgggcc cgcggggccg ccgcagatac tacctgacca gagacccaac   8820
cactccactc gcccgggctg cctgggaaac agttagacac tcccctatca attcatggct   8880
gggaaacatc atccagtatg ctccaaccat atgggttcgc atggtcctaa tgacacactt   8940
cttctccatt ctcatggtcc aagacaccct ggaccagaac ctcaactttg agatgtatgg   9000
atcagtatac tccgtgaatc ctttggacct tccagccata attgagaggt tacacgggct   9060
tgacgccttt tctatgcaca catactctca ccacgaactg acgcgggtgg cttcagccct   9120
cagaaaactt ggggcgccac ccctcagggt gtggaagagt cgggctcgcg cagtcagggc   9180
gtccctcatc tcccgtggag ggaaagcggc cgtttgcggc cgatatctct tcaattgggc   9240
ggtgaagacc aagctcaaac tcactccatt gccggaggcg cgcctactgg acttatccag   9300
ttggttcacc gtcggcgccg gcgggggcga catttttcac agcgtgtcgc gcgcccgacc   9360
ccgctcatta ctcttcggcc tactcctact tttcgtaggg gtaggcctct tcctactccc   9420
cgctcggtag agcggcacac actaggtaca ctccatagct aactgttcct tttttttttt   9480
tttttttttt tttttttttt tttttttttt ttcttttttt tttttttccc tctttcttcc   9540
cttctcatct tattctactt tctttcttgg tggctccatc ttagccctag tcacggctag   9600
ctgtgaaagg tccgtgagcc gcatgactgc agagagtgcc gtaactggtc tctctgcaga   9660
tcatgt                                                              9666
```

<210> SEQ ID NO 5
<211> LENGTH: 9666
<212> TYPE: DNA
<213> ORGANISM: Hepatitis C virus

```
<400> SEQUENCE: 5
acctgcccct aatagggggcg acactccgcc atgaatcact ccctgtgag gaactactgt    60 cttcacgcag aaagcgccta gccatggcgt tagtatgagt gtcgtacagc ctccaggccc   120 cccctcccg ggagagccat agtggtctgc ggaaccggtg agtacaccgg aattgccggg   180
aagactgggt cctttcttgg ataaaccac tctatgcccg gccatttggg cgtgccccccg   240 caagactgct agccgagtag cgttgggttg cgaaaggcct tgtggtactg cctgataggg   300
cgcttgcgag tgccccggga ggtctcgtag accgtgcacc atgagcacga atcctaaacc   360
tcaaagaaaa accaaacgta acaccaaccg tcgcccacag gacgtcaagt tcccgggtgg   420
cggtcagatc gttggtggag tttacttgtt gccgcgcagg ggcctagat tgggtgtgcg   480 cgcgacgagg aagacttccg agcggtcgca acctcgaggt agacgtcagc ctatccccaa   540
ggcacgtcgg cccgagggca ggacctgggc tcagcccggg tacccttggc ccctctatgg   600
caatgagggt tgcgggtggg cgggatggct cctgtctccc cgtggctctc ggcctagctg   660
ggcccccaca gaccccggc gtaggtcgcg caatttgggt aaggtcatcg ataccttac    720 gtgcggcttc gccgacctca tggggtacat accgctcgtc ggcgcccctc ttggaggcgc   780
tgccagggcc ctggcgcatg gcgtccgggt tctggaagac ggcgtgaact atgcaacagg   840
gaaccttcct ggttgctctt tctctatctt ccttctggcc ctgctctctt gcctgactgt   900
gcccgcttca gcctaccaag tgcgcaattc ctcgggcctt taccatgtca ccaatgattg   960
ccctaactcg agtattgtgt acgaggcggc cgatgccatc ctgcacactc cggggtgtgt  1020
cccttgcgtt cgcgagggta acgcctcgag gtgttgggtg gcggtgaccc ccacggtggc  1080
caccagggac ggcaaactcc ccacaacgca gcttcgacgt catatcgatc tgcttgtcgg  1140
gagcgccacc ctctgctcgg ccctctacgt gggggacctg tgcgggtctg tctttcttgt  1200
tggtcaactg tttaccttct ctcccaggcg ccactgacg acgcaagact gcaattgttc   1260
tatctatccc ggccatataa cgggtcatcg catggcatgg gatatgatga tgaactggtc  1320
ccctacggca gcgttggtgg tagctcagct gctccggatc ccacaagcca tcatggacat  1380
gagcgctggt gctcactggg gagtcctggc gggcatagcg tatttctcca tggtggggaa  1440
ctgggcgaag gtcctggtag tgctgctgct atttgccggc gtcgacgcgg aaacccacgt  1500
caccggggga agtgccggcc gcaccacggc tgggcttgtt ggtctcctta caccaggcgc  1560
caagcagaac atccaactga tcaacaccaa cggcagttgg cacatcaata gcacggcctt  1620
gaactgcaat gaaagcctta acaccggctg gttagcaggg ctcttctatc agcacaaatt  1680
caactcttca ggctgtcctg agaggttggc cagctgccga cgccttaccg attttgccca  1740
gggctggggt cctatcagtt atgccaacgg aagcggcctc gacgaacgcc cctactgctg  1800
gcactaccct ccaagacctt gtggcattgt gcccgcaaag agcgtgtgtg gcccggtata  1860
ttgcttcact cccagccccg tggtggtggg aacgaccgac aggtcgggcg cgcctaccta  1920
cagctggggt gcaaatgata cggatgtctt cgtccttaac aacaccaggc caccgctggg  1980
caattggttc ggttgtacct ggatgaactc aactggattc accaaagtgt gcggagcgcc  2040
cccttgtgtc atcggagggg tgggcaacaa caccttgctc tgccccactg attgtttccg  2100
caagcatccg gaagccacat actctcggtg cggctccggt ccctggatta cacccaggtg  2160
catggtcgac tacccgtata ggctttggca ctatccttgt accatcaatt acaccatatt  2220
caaagtcagg atgtacgtgg gagggtcga gcacaggctg gaagcggcct gcaactggac  2280
gcggggcgaa cgctgtgatc tggaagacag ggacaggtcc gagctcagcc cattgctgct  2340
```

-continued

```
gtccaccaca cagtggcagg tccttccgtg ttctttcacg accctgccag ccttgtccac    2400
cggcctcatc cacctccacc agaacattgt ggacgtgcag tacttgtacg gggtagggtc    2460
aagcatcgcg tcctgggcca ttaagtggga gtacgtcgtt ctcctgttcc tcctgcttgc    2520
agacgcgcgc gtctgctcct gcttgtggat gatgttactc atatcccaag cggaggcggc    2580
tttggagaac ctcgtaatac tcaatgcagc atccctggcc gggacgcacg tcttgtgtc     2640
cttcctcgtg ttcttctgct ttgcgtggta tctgaagggt aggtgggtgc ccggagcggt    2700
ctacgccttc tacgggatgt ggcctctcct cctgctcctg ctggcgttgc ctcagcgggc    2760
atacgcactg gacacggagg tggccgcgtc gtgtggcggc gttgttcttg tcgggttaat    2820
ggcgctgact ctgtcgccat attacaagcg ctacatcagc tggtgcatgt ggtggcttca    2880
gtattttctg accagagtag aagcgcaact gcacgtgtgg gttcccccc tcaacgtccg     2940
ggggggcgc gatgccgtca tcttactcat gtgtgttgta cacccgactc tggtatttga     3000
catcaccaaa ctactcctgg ccatcttcgg accccttgg attcttcaag ccagtttgct     3060
taaagtcccc tacttcgtgc gcgttcaagg ccttctccgg atctgcgcgc tagcgcggaa    3120
gatagccgga ggtcattacg tgcaaatggc catcatcaag ttaggggcgc ttactggcac    3180
ctatgtgtat aaccatctca cccctcttcg agactgggcg cacaacgcc tgcgagatct     3240
ggccgtggct gtggaaccag tcgtcttctc ccgaatggag accaagctca tcacgtgggg    3300
ggcagatacc gccgcgtgcg gtgacatcat caacggcttg cccgtctctg cccgtagggg    3360
ccaggagata ctgcttgggc cagccgacgg aatggtctcc aagggggtgga ggttgctggc   3420
tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcggggt tttgtggact gtttaccacg gagctggcaa     3600
caagactcta gccggcttac ggggtccggt cacgcagatg tactcgactg ctgaggggga    3660
cttggtaggc tggcccagcc cctctgggac caagtctttg gagccgtgca agtgtggagc    3720
cgtcgaccta tatctggtca cgcggaacgc tgatgtcatc ccggctcgga gacgcgggga    3780
caagcgggga gcattgctct ccccgagacc catttcgacc ttgaagggt cctcgggggg     3840
gccggtgctc tgccctaggg gccacgtcgt tgggctcttc cgagcagctg tgtgctctcg    3900
gggcgtggcc aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaacccctc ggtagctgcc accctgggt ttggggcgta     4140
cctatccaag gcacatggca tcaatcccaa cattaggact ggagtcagga ccgtgatgac    4200
cggggaggcc atcacgtact ccacatatgg caaatttctc gccgatgggg gctgcgctag    4260
cggcgcctat gacatcatca tatgcgatga atgccacgct gtggatgcta cctccattct    4320
cggcatcgga acggtccttg atcaagcaga gacagccggg gtcagactaa ctgtgctggc    4380
tacggccaca cccccgggt cagtgacaac ccccatccc gatatagaag aggtaggcct     4440
cgggcgggag ggtgagatcc ccttctatgg gagggcgatt ccctatcct gcatcaaggg    4500
agggagacac ctgattttct gccactcaaa gaaaagtgt gacgagctcg cggcggccct     4560
tcggggcatg ggcttgaatg ccgtggcata ctatagaggg ttggacgtct ccataatacc    4620
agctcaggga gatgtggtgg tcgtcgccac cgacgccctc atgacggggt acactggaga    4680
```

```
ctttgactcc gtgatcgact gcaatgtagc ggtcacccaa gctgtcgact tcagcctgga    4740
ccccaccttc actataacca cacagactgt cccacaagac gctgtctcac gcagtcagcg    4800
ccgcgggcgc acaggtagag gaagacaggg cacttatagg tatgtttcca ctggtgaacg    4860
agcctcagga atgtttgaca gtgtagtgct ttgtgagtgc tacgacgcag gggctgcgtg    4920
gtacgatctc acaccagcgg agaccaccgt caggcttaga gcgtatttca acacgcccgg    4980
cctacccgtg tgtcaagacc atcttgaatt ttgggaggca gttttcaccg gcctcacaca    5040
catagacgcc cacttcctct cccaaacaaa gcaagcgggg gagaacttcg cgtacctagt    5100
agcctaccaa gctacggtgt gcgccagagc caaggcccct cccccgtcct gggacgccat    5160
gtggaagtgc ctggcccgac tcaagcctac gcttgcgggc cccacacctc tcctgtaccg    5220
tttgggccct attaccaatg aggtcaccct cacacaccct gggacgaagt acatcgccac    5280
atgcatgcaa gctgaccttg aggtcatgac cagcacgtgg gtcctagctg aggagtcct    5340
ggcagccgtc gccgcatatt gcctggcgac tggatgcgtt tccatcatcg gccgcttgca    5400
cgtcaaccag cgagtcgtcg ttgcgccgga taaggaggtc ctgtatgagg cttttgatga    5460
gatgaaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt ggggccagac acatgtggaa    5640
cttcattagc ggcatccaat acctcgcagg attgtcaaca ctgccaggga ccccgcggt    5700
ggcttccatg atggcattca gtgccgcccc caccagtccg ttgtcgacca gtaccaccat    5760
ccttctcaac atcatgggag gctggttagc gtcccagatc gcaccacccg cggggggcac    5820
cggctttgtc gtcagtggcc tggtgggggc tgccgtgggc agcataggcc tgggtaaggt    5880
gctggtggac atcctggcag gatatggtgc gggcatttcg ggggccctcg tcgcattcaa    5940
gatcatgtct ggcgagaagc cctctatgga agatgtcatc aatctactgc ctgggatcct    6000
gtctccggga gccctggtgg tgggggtcat ctgcgcggcc attctgcgcc gccacgtggg    6060
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggacctt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttctcct gggtggacgg    6720
tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccaggggtgcc    7080
```

```
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctcccccaa ggagacgccg    7320
gacagtgggc tgagcgaga gcaccatatc agaagccctc cagcaactgg ccatcaagac    7380
cttggccag ccccctcga gcggtgatgc aggctcgtcc acggggcgg gcgccgccga       7440
atccggcggt ccgacgtccc ctggtgagcc ggcccctca gagacaggtt ccgcctcctc    7500
tatgccccc ctcgaggggg agcctggaga tccggacctg gagtctgatc aggtagagct    7560
tcaacctccc cccagggggg gggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaacccctt tgagtaactc    7740
gctgttgcga taccataaca aggtgtactg tacaacatca aagagcgcct cacagagggc    7800
taaaaaggta acttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccaccccatt ctgcaagatc caagtatgga ttcggggcca aggaggtccg    7980
cagcttgtcc gggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg ggtaagaaac cagctcgcct catcgtttac cctgacctcg cgtccgggt    8160
ctgcagaaa atggccctct atgacattac acaaaagctt cctcaggcgg taatgggagc    8220
ttcctatggc ttccagtact cccctgccca acgggtggag tatctcttga agcatgggc    8280
ggaaaagaag daccccatgg ttttttcgta tgatacccga tgcttcgact caaccgtcac    8340
tgagagagac atcaggaccg aggagtccat ataccaggcc tgctccctgc ccgaggaggc    8400
ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccagggac   8640
tgaggaggac gagcggaacc tgagagcctt cacggaggcc atgaccaggt actctgcccc    8700
tcctggtgat ccccccagac cggaatatga cctggagcta ataacatcct gttcctcaaa    8760
tgtgtctgtg gcgttgggcc cgcggggccg ccgcagatac tacctgacca gagacccaac    8820
cactccactc gccccgggctg cctgggaaac agttagacac tcccctatca attcatggct    8880
gggaaacatc atccagtatg ctccaaccat atgggttcgc atggtcctaa tgacacactt    8940
cttctccatt ctcatggtcc aagacaccct ggaccagaac ctcaactttg agatgtatgg    9000
atcagtatac tccgtgaatc ctttggacct tccagccata attgagaggt tacacgggct    9060
tgacgccttt tctatgcaca catactctca ccacgaactg acgcgggtgg cttcagccct    9120
cagaaaactt ggggcgccac ccctcaggggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcgggggcga catttttcac agcgtgtcgc gcgcccgacc    9360
ccgctcatta ctcttcggcc tactcctact tttcgtaggg gtaggcctct tcctactccc    9420
```

-continued

| | |
|---|---|
| cgctcggtag agcggcacac actaggtaca ctccatagct aactgttcct ttttttttt | 9480 |
| ttttttttt ttttttttt ttttttttt ttcttttttt ttttttccc tctttcttcc | 9540 |
| cttctcatct tattctactt tctttcttgg tggctccatc ttagccctag tcacggctag | 9600 |
| ctgtgaaagg tccgtgagcc gcatgactgc agagagtgcc gtaactggtc tctctgcaga | 9660 |
| tcatgt | 9666 |